United States Patent
Spiegel et al.

(10) Patent No.: US 10,213,501 B2
(45) Date of Patent: *Feb. 26, 2019

(54) THREE-COMPONENT-MULTISTAGE MALARIA VACCINE

(71) Applicant: Fraunhofer-Gesellschaft zur Foerderung der angewandten Forschung e.V., Munich (DE)

(72) Inventors: Holger Spiegel, Aachen (DE);
Alexander Boes, Cologne (DE);
Gueven Edgue, Aachen (DE);
Veronique Beiss, Aachen (DE);
Markus Sack, Alsdorf (DE); Andreas Reimann, Krefeld (DE); Rainer Fischer, Aachen (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/509,409

(22) PCT Filed: Sep. 2, 2015

(86) PCT No.: PCT/EP2015/070044
§ 371 (c)(1),
(2) Date: Mar. 7, 2017

(87) PCT Pub. No.: WO2016/037916
PCT Pub. Date: Mar. 17, 2016

(65) Prior Publication Data
US 2017/0252420 A1      Sep. 7, 2017

Related U.S. Application Data

(60) Provisional application No. 62/047,286, filed on Sep. 8, 2014.

(30) Foreign Application Priority Data

Sep. 8, 2014    (EP) ..................... 14183995

(51) Int. Cl.
*A61K 39/015*   (2006.01)
*C07K 14/445*   (2006.01)
*C12N 15/62*    (2006.01)
*C07K 16/20*    (2006.01)
*A61K 39/00*    (2006.01)

(52) U.S. Cl.
CPC .......... *A61K 39/015* (2013.01); *C07K 14/445* (2013.01); *C07K 16/205* (2013.01); *C12N 15/62* (2013.01); *A61K 2039/575* (2013.01); *A61K 2039/64* (2013.01); *A61K 2039/70* (2013.01); *C07K 2319/00* (2013.01); *C07K 2319/40* (2013.01); *Y02A 50/412* (2018.01)

(58) Field of Classification Search
None
See application file for complete search history.

(56) References Cited

U.S. PATENT DOCUMENTS

| | | |
|---|---|---|
| 3,791,932 A | 2/1974 | Wilhelmus et al. |
| 3,839,153 A | 10/1974 | Wilhelmus et al. |
| 3,850,578 A | 11/1974 | McConnell |
| 3,850,752 A | 11/1974 | Wilhelmus et al. |
| 3,853,987 A | 12/1974 | Dreyer |
| 3,867,517 A | 2/1975 | Ling |
| 3,879,262 A | 4/1975 | Wilhelmus et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,599,230 A | 7/1986 | Milich et al. |
| 4,599,231 A | 7/1986 | Milich et al. |
| 4,601,903 A | 7/1986 | Frasch |

(Continued)

FOREIGN PATENT DOCUMENTS

| | | |
|---|---|---|
| CN | 102559613 A | 7/2012 |
| DE | 102012013860 A1 | 1/2014 |

(Continued)

OTHER PUBLICATIONS

Barry et al. 2014 (Strategies for designing and monitoring malaria vaccines targeting diverse antigens; Frontiers in Immunology 5:1-16).*

(Continued)

*Primary Examiner* — Mary Maille Lyons
(74) *Attorney, Agent, or Firm* — Wagenknecht IP Law Group PC

(57) ABSTRACT

The technology provided herein relates to novel malaria vaccines composed of different recombinant proteins, in particular recombinant fusion proteins comprising several different *Plasmodium falciparum* antigens from the pre-erythrocytic, the blood, and the sexual parasite main stages. The proteins may be used in a mixture vaccine formulation to elicit protective immune responses in humans. Nucleic acid molecules encoding said recombinant proteins, vectors and host cells containing the nucleic acids and methods for preparation and producing such proteins are also disclosed, as well as antibodies induced or generated by the use of said malaria vaccines and the use of such antibodies or recombinant derivatives for passive immunotherapy.

5 Claims, 6 Drawing Sheets

Specification includes a Sequence Listing.

(56) References Cited

U.S. PATENT DOCUMENTS

| | | | |
|---|---|---|---|
| 4,608,251 | A | 8/1986 | Mia |
| 4,666,828 | A | 5/1987 | Gusella |
| 4,683,202 | A | 7/1987 | Mullis |
| 4,801,531 | A | 1/1989 | Frossard |
| 4,879,219 | A | 11/1989 | Wands et al. |
| 5,011,771 | A | 4/1991 | Bellet et al. |
| 5,192,659 | A | 3/1993 | Simons |
| 5,272,057 | A | 12/1993 | Smulson et al. |
| 5,281,521 | A | 1/1994 | Trojanowski et al. |
| 2013/0216570 | A1 | 8/2013 | Schneerson et al. |

FOREIGN PATENT DOCUMENTS

| | | |
|---|---|---|
| WO | 2007027860 A2 | 3/2007 |
| WO | 2007/041216 A2 | 4/2007 |
| WO | 2010/037063 A2 | 9/2009 |
| WO | 2012047679 A2 | 4/2012 |
| WO | 2015/144874 A1 | 10/2015 |

OTHER PUBLICATIONS

Greenspan et al. 1999 (Defining epitopes: It's not as easy as it seems; Nature Biotechnology,17:936-937). (Year: 1999).*
Richie et al. 2002 (Progress and challenges for malaria vaccines; Nature 415: 694-701). (Year: 2002).*
Barry et al. 2014 (Strategies for designing and monitoring malaria vaccines targeting diverse antigens; Frontiers in Immunology; vol. 5, article 359: 1-16). (Year: 2014).*
Ockenhouse et al. 1998 (Phase II/Ia safety, immunogenicity, and efficacy trial of NYVAC-Pf7, a pox-vectored, multiantigen, multi-stage vaccine Plasmodium falciparum malaria; Journal of Infectious Diseases; 177:1664-1673). (Year: 1998).*
Remarque et al. 2008 (A Diversity-Covering Approach to Immunization with Plasmodium falciparum Apical Membrane Antigen 1 Induces Broader Allelic Recognition and Growth Inhibition Response in Rabbits ; Infection and Immunity 76(6): 2660-2670). (Year: 2008).*
Altschul et al. "Basic Local Alignment Search Tool," Journal of Molecular Biology, 1990, 215:403-410.
Ausubel et al. "Current Protocols in Molecular Biology," Molecular Reproduction and Development, 1989, 1:146.
Beier et al. "Effects of Para-aminobenzoic Acid, Insulin, and Gentamicin on Plasmodium Falciparum Development in Anopheline Mosquitoes (Diptera: Culicidae)," Journal of Medical Entomology, 1994, 31(4)561-565.
Bishop et al. "Experiments Upon the Feeding of Aedes Aegypti Through Animal Membranes with a View to Applying the Method to the Chemotherapy of Malaria," Parasitology, 1946, 37:85-100.
Black et al. "Apical Location of a Novel EGF-like Domain-Containing Protein of Plasmodium Falciparum," Molecular & Biochemical Parasitology, 2003, 127(1)59-68.
Black et al. "Merozoite Surface Protein 8 of Plasmodium Falcipuarum Contains Two Epidermal Growth Factor-Like Domains," Molecular & Biochemical Parasitology, 2001, 114:217-226.
Blackman et al. "Proteolytic Processing of the Plasmodium Falciparum Merozoite Surface Protein-1 Produces a Membrane-Bound Fragment Containing Two Epidermal Growth Factor-Like Domains," Molecular & Biochemical Parasitology, 1991, 49(1)29-34.
Boes et al. "Affinity Purification of a Framework 1 Engineered Mouse/Human Chimeric IgA2 Antibody From Tobacco," Biotechnology and Bioengineering, 2011, 108(12)2804-14.
Chothia et al. "Conformations of Immunoglobulin Hypervariable Regions," Nature, 1989, 342:877-883.
Schwartz et al. "Atlas of Protein Sequence and Structure," 1978, National Biomedical Research, 5(Supp 3)353-358.
Epping et al. "An Epitope Recognised by Inhibitory Monoclonal Antibodies that React with a 51 Kilodalton Merozoite Surface Antigen in Plasmodium Falciparum," Molecular & Biochemical Parasitology, 1988, 28(1)1-10.
Furie et al. "The Molecular Basis of Blood Coagulation," Cell, 1988, 53(4)505-518.
Bisaro et al. "Communications in Molecular Biology Viral Vectors," Cold Spring Harbor Laboratory, 1988, pp. 172-189, Cold Spring Harbor, NY.
Gosselin et al. "Enhanced Antigen Presentation Using Human Fc Gamma Receptor (Monocyte/Macrophage)—Specific Immunogens," Journal of Immunology, 1992, 149(11)3477-3481.
Grierson et al. "Plant Viruses," Plant Molecular Biology, 1988, pp. 126-146, Blackie, London.
Hugel et al. "Release of Malaria Circumsporozoite Protein into the Host Cell Cytoplasm and Interaction with Ribosomes," Molecular & Biochemical Parasitology, 1996, 81(2)151-170.
Ifediba et al. "Complete In Vitro Maturation of Plasmodium Falciparum Gametocytes," Nature, 1981, 294(5839) 364-366.
Kaslow et al. "A Vaccine Candidate from the Sexual Stage of Human Malaria that Contains EGF-Like Domains," Nature, 1988, 333(6168)74-76.
Makler et al. "Parasite Lactate Dehydrogenase as an Assay for Plasmodium Falciparum Drug Sensitivity," The American Journal of Tropical Medicine and Hygiene, 1993, 48(6)739-741.
Marshall et al. "Close Linkage of Three Merozoite Surface Protein Genes on Chromosome 2 of Plasmodium Falciparum," Molecular & Biochemical Parasitology, 1998, 94(1)13-25.
McCormick et al. "Sporozoite Invasion Assay," Methods in Malaria Research, 5th Edition, Moll et al., Eds, 2008, MR4/ATCC Manassas, Virginia. BioMalPar Paris, France, pp. 138-140.
Pachebat et al. "The 22 kDa Component of the Protein Complex on the Surface of Plasmodium Falciparum Merozoites is Derived from a Larger Precursor, Merozoite Surface Protein 7," Molecular & Biochemical Parasitology, 2001, 117:83-89.
Patarroyo et al. "A Synthetic Vaccine Protects Humans Against Challenge with Asexual Blood Stages of Plasmodium Falciparum Malaria," Nature, 1988, 332(6160)158-161.
Rao et al. "Plant Cell Cultures: Chemical Factories of Secondary Metabolites." Biotechnology Advances 2002, 20(2) 101-153.
Rothberg et al. "Slit: An EGF-Homologous Locus of D. Melanogaster Involved in the Development of the Embryonic Central Nervous System," Cell, 1988, 55(6)1047-1059.
Taylor, W.R. "The Classification of Amino Acid Conservation," Journal of Theoretical Biology, 1986, 119:205-218.
Trucco et al. "The Merozoite Surface Protein 6 Gene Codes for a 36 kDa Protein Associated with the Plasmodium Falciparum Merozoite Surface Protein-1 Complex," Molecular & Biochemical Parasitology, 2001,112:91-101.
Tucker, R.P. "The Thrombospondim Type 1 Repeat Family," International Journal of Biochemistry & Cell Biology, 2004,36:969-974.
Wong et al. "Heating Greatly Speeds Coomassie Blue Staining and Destaining," Biotechniques, 2000, 28(3)426-432.
Tsuboi et al. "Wheat Germ Cell-Free System-Based Production of Malaria Proteins for Discovery of Novel Vaccine Candidates," Infection and Immunity, Apr. 2008, 76(4)1702-1708.
Crompton et al. "Advances and Challenges in Malaria Vaccine Development," The Journal of Clinical Investigation, Dec. 2010, 120(12)4168-4178.
PCT/EP2015/056693 International Search Report dated Jul. 27, 2015.
PCT/EP2015/070044 International Search Report dated Apr. 11, 2015.
Faber et al. "Diversity covering AMA1-MSP119 Fusion Proteins as Malaria Vaccines." Infection and Immunity, May 2013, 81(5)1479-1490.
Barry and Arnott, "Strategies for Designing and Monitoring Malaria Vaccines Targeting Diverse Antigens." Frontiers in Immunology, Jul. 28, 2014, 5(359)1-16.
Arama and Troye-Blomberg, "The Path of Malaria Vaccine Development: Challenges and Perspectives." Journal of Internal Medicine, May 18, 2014, 275(5)456-466.
Srinivasan et al. "Immunization with a Functional Protein Complex Required for Erythrocyte Invasion Protects Against Lethal Malaria." Proceedings of the National Academy of Sciences, Jul. 15, 2014, 111(28)10311-10316.

(56) References Cited

OTHER PUBLICATIONS

Kumar et al. "Potent Malaria Transmission-Blocking Antibody Responses Elicited by Plasmodium falciparum Pfs25 Expressed in *Escherichia coli* after Successful Protein Refolding." Infection and Immunity, Apr. 1, 2014, 82(4) 1453-1459.
Jones et al. "A Plant-Produced Pfs25 VLP Malaria Vaccine Candidate Induces Persistent Transmission Blocking Antibodies against Plasmodium falciparum in Immunized Mice." Plos One, 8(11)e79538(1-10).
Tamminga et al. "Human Adenovirus 5-vectored Plasmodium falciparum NMRC-M3V-Ad-PfCA Vaccine Encoding CSP and AMA1 is Safe, Well-Tolerated and Immunogenic But Does Not Protect Against Controlled Human Malaria Infection." Human Vaccines & Immunotherapeutics, Oct. 4, 2013, 9(10)2165-2177.
Appella et al. "The Receptor-Binding Sequence of Urokinase. A Biological Function for the Growth-Factor Module of Proteases," The Journal of Biological Chemistry, 1987, 262(10)4437-4440.
Bergmann-Leitner et al. "Immunization with Pre-erythrocytic Antigen CelTOS from Plasmodium Falciparum Elicits Cross-Species Protection Against Heterologous Challenge with Plasmodium Berghei," PLoS One, 2010, 5(8)e12294.
Knust et al. "EGF Homologous Sequences Encoded in the Genome of *Drosophila melanogaster*, and their Relation to Neurogenic Genes," The EMBO Journal, 1987, 6(3)761-766.
Kurosawa et al. "A 10-kDa Cyanogen Bromide Fragment from the Epidermal Growth Factor Homology Domain of Rabbit Thrombomodulin Contains the Primary Thrombin Binding Site," The Journal of Biological Chemistry, 1988, 263(13)5993-5996.
Rees et al. "The Role of Beta-Hydroxyaspartate and Adjacent Carboxylate Residues in the First EGF Domain of Human Factor IX," The Embo Journal, 1988, 7(7)2053-2061.
Sudhof et al. "The LDL Receptor Gene: A Mosaic of Exons Shared with Different Proteins," Science, 1985, 228(4701)815-822.
Suzuki et al. "Structure and Expression of Human Thrombomodulin, a Thrombin Receptor on Endothelium Acting as a Cofactor for Protein C Activation," The EMBO Journal, 1987, 6(7)1891-1897.
Brochet et al. "IMGTN-QUEST: The Highly Customized and Integrated System for IG and TR Standardized V-J and V-D-J Sequence Analysis," Nucleic Acids Research, 2008, 36:W503-508.
Chen et al. "An EGF-Like Protein Forms a Complex with PfRh5 and is Required for Invasion of Human Erythrocytes by Plasmodium Falciparum," PLoS Pathogens, 2011, 7(9)e1102199.
Garcia-Basteiro et al. "Approaching the Target: the Path Towards an Effective Malaria Vaccine," Mediterranean Journal of Hematology and Infectious Diseases, 2012, 4(1)e2012015.
Geysen et al. "Use of Peptide Synthesis to Probe Viral Antigens for Epitopes to a Resolution of a Single Amino Acid," Proceedings of the National Academy of Sciences of the United States of America, 1984, 81:3998-4002.
Kriuki et al. "Plasmodium Falciparum: Purification of the Various Gametocyte Developmental Stages from In Vitro-Cultivated Parasites," The American Society of Tropical Medicine and Hygiene, 1998, 59(4)505-508.
Kusi et al. "Immunization with Different PfAMA1 Alleles in Sequence Induces Clonal Imprint Humoral Responses that are Similar to Responses Induced by the Same Alleles as a Vaccine Cocktail in Rabbits," Malaria Journal, 2011, 10(40)1-11.
Mahajan et al. "Multiple Antigen Peptide Vaccines Against Plasmodium Falciparum Malaria," Infection and Immunity, 2010, 78(11)4613-4624.
Marshall et al. "A Second Merozoite Surface Protein (MSP-4) of Plasmodium Falciparum that Contains an Epidermal Growth Factor-Like Domain," Infection and Immunity, 1997, 65(11)4460-4467.

Pradel et al. "A Multidomain Adhesion Protein Family Expressed in Plasmodium Falciparum is Essential for Transmission to the Mosquito," The Journal of Experimental Medicine, 2004, 199(11)1533-1544.
Pradel et al. "Malaria Sporozoites Actively Enter and Pass Through Rat Kupffer Cells Prior to Hepatocyte Invasion," Hepatology, 2001, 33(5)1154-1165.
Plassmeyer et al. "Structure of the Plasmodium Falciparum Circumsporozoite Protein, A Leading Malaria Vaccine candidate." The Journal of Biological Chemistry, 2009, 284(39)26951-26963.
Rathore et al. "Molecular Mechanism of Host Specificity in Plasmodium Falciparum Infection: Role of Circumsporozoite Protein," The Journal of Biological Chemistry, 2003, 278(42)40905-40910.
Richards et al. "The Future for Blood-Stage Vaccines Against Malaria," Immunology and Cell Biology, 2009, 87(5)377-390.
Roestenberg et al. "Safety and Immunogenicity of a Recombinant Plasmodium Falciparum AMA1 Malaria Vaccine Adjuvanted with Alhydrogel, Montanide ISA 720 or AS02," PloS one, 2008, 3(12)e3960.
Sack et al. "Functional Analysis of the Broadly Neutralizing Human Anti-HIV-1 Antibody 2F5 Produced in Transgenic BY-2 Suspension Cultures," The FASEB Journal, 2007, 21(8)1655-1664.
Schwartz et al. "A Review of Malaria Vaccine Clinical Projects Based on the WHO Rainbow Table," Malaria Journal, 2012, 11(11)1-22.
Smith et al. "Comparison of Biosequences," Advances in Applied Mathematics, 1981, 2:482-489.
Srinivasan et al. "Binding of Plasmodium Merozoite Proteins RON2 and AMA1 Triggers Commitment to Invasion," Proceedings of the National Academy of Sciences of the United States of America, 2011, 108(32):13275-13280.
Tachibana et al. "N-terminal Prodomain of Pfs230 Synthesized Using a Cell-Free System is Sufficient to Induce Complement-Dependent Malaria Transmission-Blocking Activity," Clinical and Vaccine Immunology, Aug. 2011, 18(8)1343-50.
Tan et al. "Crystal Structure of the TSP-1 Type 1 Repeats: A Novel Layered Fold and Its Biological Implication," The Journal of Cell Biology, 2002, 159(2)373-382.
Tossavainen et al. "The Layered Fold of the TSR Domain of P. Falciparum TRAP Contains a Heparin Binding Site," Protein Science, 2006, 15(7)1760-1768.
Uchime et al. "Analysis of the Conformation and Function of the Plasmodium falciparum Merozoite Proteins MTRAP and PTRAMP," Eukaryotic Cell, 2012, 11(5)615-625.
Vaquero et al. "Transient Expression of a Tumor-Specific Single-Chain Fragment and a Chimeric Antibody in Tobacco Leaves," Proceedings of the National Academy of Sciences of the United States of America, 1999, 96(20)11128-11133.
Wasmuth et al. "The Origins of Apicomplexan Sequence Innovation," Genome Research, 2009, 19(7)1202-1213.
Anderson, Laura Fay, "Malaria Proteins Implicated in Host-Parasite," PhD Thesis, 2006, University of Edinburgh, https://www.researchgate.net/profile/Laura_Anderson23/publication/292609039_Malaria_Proteins_Implicated_in_Host-Parasite_Interactions/links/56d0759e08ae059e375d433e/Malaria-Proteins-Implicated-in-Host-Parasite-Interactions.pdf?origin=publication_detail, retrieved on Nov. 2, 2017.
Boes et al. "Analysis of a Multi-component Multi-stage Malaria Vaccine Candidate—Tackling the Cocktail Challenge," Plos One, Jul. 6, 2015, 10(7):e0131456.
Imam et al. "Comparative Immunogenicities of Full-Length Plasmodium Falciparum Merozoite Surface Protein 3 and a 24-Kilodalton N-Terminal Fragment," Clinical and Vaccine Immunology, Aug. 2011, 18(8):1221-1228.
Reiling et al. "Evidence that the Erythrocyte Invasion Ligand PfRh2 is a Target of Protective Immunity against Plasmodium Falciparum Malaria," The Journal of Immunology, 2010, 185:6157-6167.

* cited by examiner

SEQUENCE LISTING

```
<160> NUMBER OF SEQ ID NOS: 12

<210> SEQ ID NO 1
<211> LENGTH: 521
<212> TYPE: PRT
<213> ORGANISM: Plasmodium falciparum

<400> SEQUENCE: 1

Gln Asn Tyr Trp Glu His Pro Tyr Gln Lys Ser Asp Val Tyr His Pro
1               5                   10                  15

Ile Asn Glu His Arg Glu His Pro Lys Glu Tyr Glu Tyr Pro Leu His
            20                  25                  30

Gln Glu His Thr Tyr Gln Gln Glu Asp Ser Gly Glu Asp Glu Asn Thr
        35                  40                  45

Leu Gln His Ala Tyr Pro Ile Asp His Glu Gly Ala Glu Pro Ala Pro
    50                  55                  60

Gln Glu Gln Asn Leu Phe Ser Ser Ile Glu Ile Val Glu Arg Ser Asn
65                  70                  75                  80

Tyr Met Gly Asn Pro Trp Thr Glu Tyr Met Ala Lys Tyr Asp Ile Glu
                85                  90                  95

Glu Val His Gly Ser Gly Ile Arg Val Asp Leu Gly Glu Asp Ala Glu
            100                 105                 110

Val Ala Gly Thr Gln Tyr Arg Leu Pro Ser Gly Lys Cys Pro Val Phe
        115                 120                 125

Gly Lys Gly Ile Ile Glu Asn Ser Gln Thr Thr Phe Leu Thr Pro
    130                 135                 140

Val Ala Thr Glu Asn Gln Asp Leu Lys Asp Gly Gly Phe Ala Phe Pro
145                 150                 155                 160

Pro Thr Lys Pro Leu Met Ser Pro Met Thr Leu Asp Gln Met Arg His
                165                 170                 175

Phe Tyr Lys Asp Asn Glu Tyr Val Lys Asn Leu Asp Glu Leu Thr Leu
            180                 185                 190

Cys Ser Arg His Ala Gly Asn Met Asn Pro Asp Asn Asp Lys Asn Ser
        195                 200                 205

Asn Tyr Lys Tyr Pro Ala Val Tyr Asp Asp Lys Asp Lys Lys Cys His
    210                 215                 220

Ile Leu Tyr Ile Ala Ala Gln Glu Asn Asn Gly Pro Arg Tyr Cys Asn
```

```
            225                 230                 235                 240
Lys Asp Glu Ser Lys Arg Asn Ser Met Phe Cys Phe Arg Pro Ala Lys
                245                 250                 255

Asp Lys Ser Phe Gln Asn Tyr Val Tyr Leu Ser Lys Asn Val Val Asp
                260                 265                 270

Asn Trp Glu Lys Val Cys Pro Arg Lys Asn Leu Glu Asn Ala Lys Phe
                275                 280                 285

Gly Leu Trp Val Asp Gly Asn Cys Glu Asp Ile Pro His Val Asn Glu
            290                 295                 300

Phe Ser Ala Asn Asp Leu Phe Glu Cys Asn Lys Leu Val Phe Glu Leu
305                 310                 315                 320

Ser Ala Ser Asp Gln Pro Lys Gln Tyr Glu Gln His Leu Thr Asp Tyr
                325                 330                 335

Glu Lys Ile Lys Glu Gly Phe Lys Asn Lys Asn Ala Asp Met Ile Arg
                340                 345                 350

Ser Ala Phe Leu Pro Thr Gly Ala Phe Lys Ala Asp Arg Tyr Lys Ser
                355                 360                 365

His Gly Lys Gly Tyr Asn Trp Gly Asn Tyr Asn Arg Lys Thr Gln Lys
            370                 375                 380

Cys Glu Ile Phe Asn Val Lys Pro Thr Cys Leu Ile Asn Asp Lys Ser
385                 390                 395                 400

Tyr Ile Ala Thr Thr Ala Leu Ser His Pro Ile Glu Val Glu His Asn
                405                 410                 415

Phe Pro Cys Ser Leu Tyr Lys Asp Glu Ile Lys Lys Glu Ile Glu Arg
                420                 425                 430

Glu Ser Lys Arg Ile Lys Leu Asn Asp Asn Asp Glu Gly Asn Lys
            435                 440                 445

Lys Ile Ile Ala Pro Arg Ile Phe Ile Ser Asp Lys Asp Ser Leu
450                 455                 460

Lys Cys Pro Cys Asp Pro Glu Ile Val Ser Gln Ser Thr Cys Asn Phe
465                 470                 475                 480

Phe Val Cys Lys Cys Val Glu Lys Arg Ala Glu Val Thr Ser Asn Asn
                485                 490                 495

Glu Val Val Lys Glu Glu Tyr Lys Asp Glu Tyr Ala Asp Ile Pro
                500                 505                 510

Glu His Lys Pro Thr Tyr Asp Lys Met
            515                 520
```

<210> SEQ ID NO 2
<211> LENGTH: 521
<212> TYPE: PRT
<213> ORGANISM: Plasmodium falciparum

<400> SEQUENCE: 2

```
Gln Asn Tyr Trp Glu His Pro Tyr Gln Lys Ser Asp Val Tyr His Pro
1               5                   10                  15

Ile Asn Glu His Arg Glu His Pro Lys Glu Tyr Glu Tyr Pro Leu His
                20                  25                  30

Gln Glu His Thr Tyr Gln Gln Glu Asp Ser Gly Glu Asp Glu Asn Thr
            35                  40                  45

Leu Gln His Ala Tyr Pro Ile Asp His Glu Gly Ala Glu Pro Ala Pro
        50                  55                  60

Gln Glu Gln Asn Leu Phe Ser Ser Ile Glu Ile Val Glu Arg Ser Asn
65              70                  75                  80
```

```
Tyr Met Gly Asn Pro Trp Thr Glu Tyr Met Ala Lys Tyr Asp Ile Glu
                85                  90                  95

Glu Val His Gly Ser Gly Ile Arg Val Asp Leu Gly Glu Asp Ala Glu
            100                 105                 110

Val Ala Gly Thr Gln Tyr Arg Leu Pro Ser Gly Lys Cys Pro Val Phe
            115                 120                 125

Gly Lys Gly Ile Ile Ile Glu Asn Ser Gln Thr Thr Phe Leu Lys Pro
130                 135                 140

Val Ala Thr Gly Asn Gln Asp Leu Lys Asp Gly Gly Phe Ala Phe Pro
145                 150                 155                 160

Pro Thr Asn Pro Leu Ile Ser Pro Met Thr Leu Asn Gly Met Arg Asp
                165                 170                 175

Phe Tyr Lys Asn Asn Glu Tyr Val Lys Asn Leu Asp Glu Leu Thr Leu
            180                 185                 190

Cys Ser Arg His Ala Gly Asn Met Asn Pro Asp Asn Asp Glu Asn Ser
            195                 200                 205

Asn Tyr Lys Tyr Pro Ala Val Tyr Asp Tyr Asn Asp Lys Lys Cys His
        210                 215                 220

Ile Leu Tyr Ile Ala Ala Gln Glu Asn Asn Gly Pro Arg Tyr Cys Asn
225                 230                 235                 240

Lys Asp Glu Ser Lys Arg Asn Ser Met Phe Cys Phe Arg Pro Ala Lys
                245                 250                 255

Asp Lys Leu Phe Glu Asn Tyr Val Tyr Leu Ser Lys Asn Val Val His
            260                 265                 270

Asn Trp Glu Glu Val Cys Pro Arg Lys Asn Leu Glu Asn Ala Lys Phe
        275                 280                 285

Gly Leu Trp Val Asp Gly Asn Cys Glu Asp Ile Pro His Val Asn Glu
290                 295                 300

Phe Ser Ala Asn Asp Leu Phe Glu Cys Asn Lys Leu Val Phe Glu Leu
305                 310                 315                 320

Ser Ala Ser Asp Gln Pro Lys Gln Tyr Glu Gln His Leu Thr Asp Tyr
                325                 330                 335

Glu Lys Ile Lys Glu Gly Phe Lys Asn Lys Asn Ala Asp Met Ile Arg
            340                 345                 350

Ser Ala Phe Leu Pro Thr Gly Ala Phe Lys Ala Asp Arg Tyr Lys Ser
            355                 360                 365

Arg Gly Lys Gly Tyr Asn Trp Gly Asn Tyr Asn Arg Lys Thr Gln Lys
        370                 375                 380

Cys Glu Ile Phe Asn Val Lys Pro Thr Cys Leu Ile Asn Asp Lys Ser
385                 390                 395                 400

Tyr Ile Ala Thr Thr Ala Leu Ser His Pro Ile Glu Val Glu Asn Asn
                405                 410                 415

Phe Pro Cys Ser Leu Tyr Lys Asn Glu Ile Met Lys Glu Ile Glu Arg
            420                 425                 430

Glu Ser Lys Arg Ile Lys Leu Asn Asp Asn Asp Glu Gly Asn Lys
            435                 440                 445

Lys Ile Ile Ala Pro Arg Ile Phe Ile Ser Asp Lys Asp Ser Leu
450                 455                 460

Lys Cys Pro Cys Asp Pro Glu Met Val Ser Gln Ser Thr Cys Arg Phe
465                 470                 475                 480

Phe Val Cys Lys Cys Val Glu Arg Arg Ala Glu Val Thr Ser Asn Asn
            485                 490                 495

Glu Val Val Val Lys Glu Glu Tyr Lys Asp Glu Tyr Ala Asp Ile Pro
```

```
                        500             505             510
Glu His Lys Pro Thr Tyr Asp Asn Met
        515                 520

<210> SEQ ID NO 3
<211> LENGTH: 521
<212> TYPE: PRT
<213> ORGANISM: Plasmodium falciparum

<400> SEQUENCE: 3

Gln Asn Tyr Trp Glu His Pro Tyr Gln Lys Ser Asp Val Tyr His Pro
1               5                   10                  15

Ile Asn Glu His Arg Glu His Pro Lys Glu Tyr Glu Tyr Pro Leu His
            20                  25                  30

Gln Glu His Thr Tyr Gln Gln Glu Asp Ser Gly Glu Asp Glu Asn Thr
        35                  40                  45

Leu Gln His Ala Tyr Pro Ile Asp His Glu Gly Ala Glu Pro Ala Pro
    50                  55                  60

Gln Glu Gln Asn Leu Phe Ser Ser Ile Glu Ile Val Glu Arg Ser Asn
65                  70                  75                  80

Tyr Met Gly Asn Pro Trp Thr Glu Tyr Met Ala Lys Tyr Asp Ile Glu
                85                  90                  95

Glu Val His Gly Ser Gly Ile Arg Val Asp Leu Gly Glu Asp Ala Glu
            100                 105                 110

Val Ala Gly Thr Gln Tyr Arg Leu Pro Ser Gly Lys Cys Pro Val Phe
        115                 120                 125

Gly Lys Gly Ile Ile Ile Glu Asn Ser Lys Thr Thr Phe Leu Thr Pro
130                 135                 140

Val Ala Thr Glu Asn Gln Asp Leu Lys Asp Gly Gly Phe Ala Phe Pro
145                 150                 155                 160

Pro Thr Glu Pro Leu Met Ser Pro Met Thr Leu Asp Asp Met Arg Asp
                165                 170                 175

Leu Tyr Lys Asp Asn Lys Tyr Val Lys Asn Leu Asp Glu Leu Thr Leu
            180                 185                 190

Cys Ser Arg His Ala Gly Asn Met Ile Pro Asp Asn Asp Lys Asn Ser
        195                 200                 205

Asn Tyr Lys Tyr Pro Ala Val Tyr Asp Tyr Glu Asp Lys Lys Cys His
    210                 215                 220

Ile Leu Tyr Ile Ala Ala Gln Glu Asn Asn Gly Pro Arg Tyr Cys Asn
225                 230                 235                 240

Lys Asp Gln Ser Lys Arg Asn Ser Met Phe Cys Phe Arg Pro Ala Lys
                245                 250                 255

Asp Ile Ser Phe Gln Asn Tyr Val Tyr Leu Ser Lys Asn Val Val Asp
            260                 265                 270

Asn Trp Glu Lys Val Cys Pro Arg Lys Asn Leu Gln Asn Ala Lys Phe
        275                 280                 285

Gly Leu Trp Val Asp Gly Asn Cys Glu Asp Ile Pro His Val Asn Glu
    290                 295                 300

Phe Ser Ala Ile Asp Leu Phe Glu Cys Asn Lys Leu Val Phe Glu Leu
305                 310                 315                 320

Ser Ala Ser Asp Gln Pro Lys Gln Tyr Glu Gln His Leu Thr Asp Tyr
                325                 330                 335

Glu Lys Ile Lys Glu Gly Phe Lys Asn Lys Asn Ala Asp Met Ile Arg
            340                 345                 350
```

```
Ser Ala Phe Leu Pro Thr Gly Ala Phe Lys Ala Asp Arg Tyr Lys Ser
            355                 360                 365

His Gly Lys Gly Tyr Asn Trp Gly Asn Tyr Thr Glu Thr Gln Lys
    370                 375                 380

Cys Glu Ile Phe Asn Val Lys Pro Thr Cys Leu Ile Asn Asp Lys Ser
385                 390                 395                 400

Tyr Ile Ala Thr Thr Ala Leu Ser His Pro Asn Glu Val Glu His Asn
                405                 410                 415

Phe Pro Cys Ser Leu Tyr Lys Asp Glu Ile Lys Glu Ile Glu Arg
                420                 425                 430

Glu Ser Lys Arg Ile Lys Leu Asn Asp Asn Asp Glu Gly Asn Lys
            435                 440                 445

Lys Ile Ile Ala Pro Arg Ile Phe Ile Ser Asp Asp Ile Asp Ser Leu
    450                 455                 460

Lys Cys Pro Cys Ala Pro Glu Ile Val Ser Gln Ser Thr Cys Asn Phe
465                 470                 475                 480

Phe Val Cys Lys Cys Val Glu Lys Arg Ala Glu Val Thr Ser Asn Asn
                485                 490                 495

Glu Val Val Val Lys Glu Glu Tyr Lys Asp Glu Tyr Ala Asp Ile Pro
                500                 505                 510

Glu His Lys Pro Thr Tyr Asp Lys Met
            515                 520

<210> SEQ ID NO 4
<211> LENGTH: 169
<212> TYPE: PRT
<213> ORGANISM: Plasmodium falciparum

<400> SEQUENCE: 4

Val Thr Val Asp Thr Val Cys Lys Arg Gly Phe Leu Ile Gln Met Ser
1               5                   10                  15

Gly His Leu Glu Cys Lys Cys Glu Asn Asp Leu Val Leu Val Asn Glu
            20                  25                  30

Glu Thr Cys Glu Glu Lys Val Leu Lys Cys Asp Glu Lys Thr Val Asn
        35                  40                  45

Lys Pro Cys Gly Asp Phe Ser Lys Cys Ile Lys Ile Asp Gly Asn Pro
    50                  55                  60

Val Ser Tyr Ala Cys Lys Cys Asn Leu Gly Tyr Asp Met Val Asn Asn
65                  70                  75                  80

Val Cys Ile Pro Asn Glu Cys Lys Asn Val Ala Cys Gly Asn Gly Lys
                85                  90                  95

Cys Ile Leu Asp Thr Ser Asn Pro Val Lys Thr Gly Val Cys Ser Cys
            100                 105                 110

Asn Ile Gly Lys Val Pro Asn Val Gln Asp Gln Lys Cys Ser Lys Asp
        115                 120                 125

Gly Glu Thr Lys Cys Ser Leu Lys Cys Leu Lys Glu Asn Glu Ala Cys
    130                 135                 140

Lys Ala Val Asp Gly Ile Tyr Lys Cys Asp Cys Lys Asp Gly Phe Ile
145                 150                 155                 160

Ile Asp Asn Glu Ala Ser Ile Cys Thr
                165

<210> SEQ ID NO 5
<211> LENGTH: 73
<212> TYPE: PRT
<213> ORGANISM: Plasmodium falciparum
```

<400> SEQUENCE: 5

Pro Ser Asp Lys His Ile Lys Glu Tyr Leu Asn Lys Ile Gln Asn Ser
1               5                   10                  15

Leu Ser Thr Glu Trp Ser Pro Cys Ser Val Thr Cys Gly Asn Gly Ile
            20                  25                  30

Gln Val Arg Ile Lys Pro Gly Ser Ala Asn Lys Pro Lys Asp Glu Leu
        35                  40                  45

Asp Tyr Ala Asn Asp Ile Glu Lys Lys Ile Cys Lys Met Glu Lys Cys
    50                  55                  60

Ser Ser Val Phe Asn Val Val Asn Ser
65                  70

<210> SEQ ID NO 6
<211> LENGTH: 95
<212> TYPE: PRT
<213> ORGANISM: Plasmodium falciparum

<400> SEQUENCE: 6

Ile Ser Gln His Gln Cys Val Lys Lys Gln Cys Pro Glu Asn Ser Gly
1               5                   10                  15

Cys Phe Arg His Leu Asp Glu Arg Glu Glu Cys Lys Cys Leu Leu Asn
            20                  25                  30

Tyr Lys Gln Glu Gly Asp Lys Cys Val Glu Asn Pro Asn Pro Ala Cys
        35                  40                  45

Asn Glu Asn Asn Gly Gly Cys Asp Ala Asp Ala Lys Cys Thr Glu Glu
    50                  55                  60

Asp Ser Gly Ser Asn Gly Lys Lys Ile Thr Cys Glu Cys Thr Lys Pro
65                  70                  75                  80

Asp Ser Tyr Pro Leu Phe Asp Gly Ile Phe Cys Ser Ser Ser Asn
                85                  90                  95

<210> SEQ ID NO 7
<211> LENGTH: 16
<212> TYPE: PRT
<213> ORGANISM: Plasmodium falciparum

<400> SEQUENCE: 7

Ser Thr Tyr Gly Lys Ala Ile Ala Val Asp Ala Phe Ile Lys Lys Ile
1               5                   10                  15

<210> SEQ ID NO 8
<211> LENGTH: 13
<212> TYPE: PRT
<213> ORGANISM: Plasmodium falciparum

<400> SEQUENCE: 8

Thr Asn Gly Ile Arg Tyr His Tyr Asp Glu Tyr Ile His
1               5                   10

<210> SEQ ID NO 9
<211> LENGTH: 769
<212> TYPE: PRT
<213> ORGANISM: Plasmodium falciparum

<400> SEQUENCE: 9

Glu Phe Gln Asn Tyr Trp Glu His Pro Tyr Gln Lys Ser Asp Val Tyr
1               5                   10                  15

His Pro Ile Asn Glu His Arg Glu His Pro Lys Glu Tyr Glu Tyr Pro
            20                  25                  30

```
Leu His Gln Glu His Thr Tyr Gln Gln Glu Asp Ser Gly Glu Asp Glu
        35                  40                  45

Asn Thr Leu Gln His Ala Tyr Pro Ile Asp His Glu Gly Ala Glu Pro
 50                      55                  60

Ala Pro Gln Glu Gln Asn Leu Phe Ser Ile Glu Ile Val Glu Arg
 65                  70                  75                  80

Ser Asn Tyr Met Gly Asn Pro Trp Thr Glu Tyr Met Ala Lys Tyr Asp
                 85                  90                  95

Ile Glu Glu Val His Gly Ser Gly Ile Arg Val Asp Leu Gly Glu Asp
                100                 105                 110

Ala Glu Val Ala Gly Thr Gln Tyr Arg Leu Pro Ser Gly Lys Cys Pro
            115                 120                 125

Val Phe Gly Lys Gly Ile Ile Ile Glu Asn Ser Gln Thr Thr Phe Leu
        130                 135                 140

Thr Pro Val Ala Thr Glu Asn Gln Asp Leu Lys Asp Gly Gly Phe Ala
145                 150                 155                 160

Phe Pro Pro Thr Lys Pro Leu Met Ser Pro Met Thr Leu Asp Gln Met
                165                 170                 175

Arg His Phe Tyr Lys Asp Asn Glu Tyr Val Lys Asn Leu Asp Glu Leu
                180                 185                 190

Thr Leu Cys Ser Arg His Ala Gly Asn Met Asn Pro Asp Asn Asp Lys
            195                 200                 205

Asn Ser Asn Tyr Lys Tyr Pro Ala Val Tyr Asp Asp Lys Asp Lys Lys
        210                 215                 220

Cys His Ile Leu Tyr Ile Ala Ala Gln Glu Asn Asn Gly Pro Arg Tyr
225                 230                 235                 240

Cys Asn Lys Asp Glu Ser Lys Arg Asn Ser Met Phe Cys Phe Arg Pro
                245                 250                 255

Ala Lys Asp Lys Ser Phe Gln Asn Tyr Val Tyr Leu Ser Lys Asn Val
                260                 265                 270

Val Asp Asn Trp Glu Lys Val Cys Pro Arg Lys Asn Leu Glu Asn Ala
            275                 280                 285

Lys Phe Gly Leu Trp Val Asp Gly Asn Cys Glu Asp Ile Pro His Val
        290                 295                 300

Asn Glu Phe Ser Ala Asn Asp Leu Phe Glu Cys Asn Lys Leu Val Phe
305                 310                 315                 320

Glu Leu Ser Ala Ser Asp Gln Pro Lys Gln Tyr Glu Gln His Leu Thr
                325                 330                 335

Asp Tyr Glu Lys Ile Lys Glu Gly Phe Lys Asn Lys Asn Ala Asp Met
            340                 345                 350

Ile Arg Ser Ala Phe Leu Pro Thr Gly Ala Phe Lys Ala Asp Arg Tyr
        355                 360                 365

Lys Ser His Gly Lys Gly Tyr Asn Trp Gly Asn Tyr Asn Arg Lys Thr
        370                 375                 380

Gln Lys Cys Glu Ile Phe Asn Val Lys Pro Thr Cys Leu Ile Asn Asp
385                 390                 395                 400

Lys Ser Tyr Ile Ala Thr Thr Ala Leu Ser His Pro Ile Glu Val Glu
                405                 410                 415

His Asn Phe Pro Cys Ser Leu Tyr Lys Asp Glu Ile Lys Lys Glu Ile
                420                 425                 430

Glu Arg Glu Ser Lys Arg Ile Lys Leu Asn Asp Asn Asp Asp Glu Gly
            435                 440                 445
```

```
Asn Lys Lys Ile Ile Ala Pro Arg Ile Phe Ile Ser Asp Asp Lys Asp
    450                 455                 460

Ser Leu Lys Cys Pro Cys Asp Pro Glu Ile Val Ser Gln Ser Thr Cys
465                 470                 475                 480

Asn Phe Phe Val Cys Lys Cys Val Glu Lys Arg Ala Glu Val Thr Ser
                485                 490                 495

Asn Asn Glu Val Val Val Lys Glu Glu Tyr Lys Asp Glu Tyr Ala Asp
            500                 505                 510

Ile Pro Glu His Lys Pro Thr Tyr Asp Lys Met Ala Ala Val Thr Val
                515                 520                 525

Asp Thr Val Cys Lys Arg Gly Phe Leu Ile Gln Met Ser Gly His Leu
530                 535                 540

Glu Cys Lys Cys Glu Asn Asp Leu Val Leu Val Asn Glu Glu Thr Cys
545                 550                 555                 560

Glu Glu Lys Val Leu Lys Cys Asp Glu Lys Thr Val Asn Lys Pro Cys
                565                 570                 575

Gly Asp Phe Ser Lys Cys Ile Lys Ile Asp Gly Asn Pro Val Ser Tyr
            580                 585                 590

Ala Cys Lys Cys Asn Leu Gly Tyr Asp Met Val Asn Asn Val Cys Ile
                595                 600                 605

Pro Asn Glu Cys Lys Asn Val Ala Cys Gly Asn Gly Lys Cys Ile Leu
            610                 615                 620

Asp Thr Ser Asn Pro Val Lys Thr Gly Val Cys Ser Cys Asn Ile Gly
625                 630                 635                 640

Lys Val Pro Asn Val Gln Asp Gln Lys Cys Ser Lys Asp Gly Glu Thr
                645                 650                 655

Lys Cys Ser Leu Lys Cys Leu Lys Glu Asn Glu Ala Cys Lys Ala Val
            660                 665                 670

Asp Gly Ile Tyr Lys Cys Asp Cys Lys Asp Gly Phe Ile Ile Asp Asn
            675                 680                 685

Glu Ala Ser Ile Cys Thr Ala Ala Pro Ser Asp Lys His Ile Lys Glu
            690                 695                 700

Tyr Leu Asn Lys Ile Gln Asn Ser Leu Ser Thr Glu Trp Ser Pro Cys
705                 710                 715                 720

Ser Val Thr Cys Gly Asn Gly Ile Gln Val Arg Ile Lys Pro Gly Ser
                725                 730                 735

Ala Asn Lys Pro Lys Asp Glu Leu Asp Tyr Ala Asn Asp Ile Glu Lys
            740                 745                 750

Lys Ile Cys Lys Met Glu Lys Cys Ser Ser Val Phe Asn Val Val Asn
            755                 760                 765

Ser

<210> SEQ ID NO 10
<211> LENGTH: 791
<212> TYPE: PRT
<213> ORGANISM: Plasmodium falciparum

<400> SEQUENCE: 10

Glu Phe Gln Asn Tyr Trp Glu His Pro Tyr Gln Lys Ser Asp Val Tyr
1               5                   10                  15

His Pro Ile Asn Glu His Arg Glu His Pro Lys Glu Tyr Glu Tyr Pro
            20                  25                  30

Leu His Gln Glu His Thr Tyr Gln Gln Glu Asp Ser Gly Glu Asp Glu
        35                  40                  45
```

```
Asn Thr Leu Gln His Ala Tyr Pro Ile Asp His Glu Gly Ala Glu Pro
    50              55              60

Ala Pro Gln Glu Gln Asn Leu Phe Ser Ser Ile Glu Ile Val Glu Arg
65              70              75              80

Ser Asn Tyr Met Gly Asn Pro Trp Thr Glu Tyr Met Ala Lys Tyr Asp
                85              90              95

Ile Glu Glu Val His Gly Ser Gly Ile Arg Val Asp Leu Gly Glu Asp
            100             105             110

Ala Glu Val Ala Gly Thr Gln Tyr Arg Leu Pro Ser Gly Lys Cys Pro
        115             120             125

Val Phe Gly Lys Gly Ile Ile Ile Glu Asn Ser Gln Thr Thr Phe Leu
130             135             140

Lys Pro Val Ala Thr Gly Asn Gln Asp Leu Lys Asp Gly Gly Phe Ala
145             150             155             160

Phe Pro Pro Thr Asn Pro Leu Ile Ser Pro Met Thr Leu Asn Gly Met
                165             170             175

Arg Asp Phe Tyr Lys Asn Asn Glu Tyr Val Lys Asn Leu Asp Glu Leu
            180             185             190

Thr Leu Cys Ser Arg His Ala Gly Asn Met Asn Pro Asp Asn Asp Glu
        195             200             205

Asn Ser Asn Tyr Lys Tyr Pro Ala Val Tyr Asp Tyr Asn Asp Lys Lys
210             215             220

Cys His Ile Leu Tyr Ile Ala Ala Gln Glu Asn Asn Gly Pro Arg Tyr
225             230             235             240

Cys Asn Lys Asp Glu Ser Lys Arg Asn Ser Met Phe Cys Phe Arg Pro
                245             250             255

Ala Lys Asp Lys Leu Phe Glu Asn Tyr Val Tyr Leu Ser Lys Asn Val
            260             265             270

Val His Asn Trp Glu Glu Val Cys Pro Arg Lys Asn Leu Glu Asn Ala
        275             280             285

Lys Phe Gly Leu Trp Val Asp Gly Asn Cys Glu Asp Ile Pro His Val
290             295             300

Asn Glu Phe Ser Ala Asn Asp Leu Phe Glu Cys Asn Lys Leu Val Phe
305             310             315             320

Glu Leu Ser Ala Ser Asp Gln Pro Lys Gln Tyr Glu Gln His Leu Thr
                325             330             335

Asp Tyr Glu Lys Ile Lys Glu Gly Phe Lys Asn Lys Asn Ala Asp Met
            340             345             350

Ile Arg Ser Ala Phe Leu Pro Thr Gly Ala Phe Lys Ala Asp Arg Tyr
        355             360             365

Lys Ser Arg Gly Lys Gly Tyr Asn Trp Gly Asn Tyr Asn Arg Lys Thr
370             375             380

Gln Lys Cys Glu Ile Phe Asn Val Lys Pro Thr Cys Leu Ile Asn Asp
385             390             395             400

Lys Ser Tyr Ile Ala Thr Thr Ala Leu Ser His Pro Ile Glu Val Glu
                405             410             415

Asn Asn Phe Pro Cys Ser Leu Tyr Lys Asn Glu Ile Met Lys Glu Ile
            420             425             430

Glu Arg Glu Ser Lys Arg Ile Lys Leu Asn Asp Asn Asp Glu Gly
        435             440             445

Asn Lys Lys Ile Ile Ala Pro Arg Ile Phe Ile Ser Asp Asp Lys Asp
450             455             460

Ser Leu Lys Cys Pro Cys Asp Pro Glu Met Val Ser Gln Ser Thr Cys
```

-continued

```
                465                 470                 475                 480
Arg Phe Phe Val Cys Lys Cys Val Glu Arg Arg Ala Glu Val Thr Ser
                    485                 490                 495

Asn Asn Glu Val Val Lys Glu Glu Tyr Lys Asp Glu Tyr Ala Asp
                500                 505                 510

Ile Pro Glu His Lys Pro Thr Tyr Asp Asn Met Ala Ala Val Thr Val
                515                 520                 525

Asp Thr Val Cys Lys Arg Gly Phe Leu Ile Gln Met Ser Gly His Leu
                530                 535                 540

Glu Cys Lys Cys Glu Asn Asp Leu Val Leu Val Asn Glu Thr Cys
545                 550                 555                 560

Glu Glu Lys Val Leu Lys Cys Asp Glu Lys Thr Val Asn Lys Pro Cys
                    565                 570                 575

Gly Asp Phe Ser Lys Cys Ile Lys Ile Asp Gly Asn Pro Val Ser Tyr
                    580                 585                 590

Ala Cys Lys Cys Asn Leu Gly Tyr Asp Met Val Asn Asn Val Cys Ile
                    595                 600                 605

Pro Asn Glu Cys Lys Asn Val Ala Cys Gly Asn Gly Lys Cys Ile Leu
                610                 615                 620

Asp Thr Ser Asn Pro Val Lys Thr Gly Val Cys Ser Cys Asn Ile Gly
625                 630                 635                 640

Lys Val Pro Asn Val Gln Asp Gln Lys Cys Ser Lys Asp Gly Glu Thr
                    645                 650                 655

Lys Cys Ser Leu Lys Cys Leu Lys Glu Asn Glu Ala Cys Lys Ala Val
                    660                 665                 670

Asp Gly Ile Tyr Lys Cys Asp Cys Lys Asp Gly Phe Ile Ile Asp Asn
                    675                 680                 685

Glu Ala Ser Ile Cys Thr Ala Ala Ile Ser Gln His Gln Cys Val Lys
                690                 695                 700

Lys Gln Cys Pro Glu Asn Ser Gly Cys Phe Arg His Leu Asp Glu Arg
705                 710                 715                 720

Glu Glu Cys Lys Cys Leu Leu Asn Tyr Lys Gln Glu Gly Asp Lys Cys
                    725                 730                 735

Val Glu Asn Pro Asn Pro Ala Cys Asn Glu Asn Asn Gly Gly Cys Asp
                        740                 745                 750

Ala Asp Ala Lys Cys Thr Glu Glu Asp Ser Gly Ser Asn Gly Lys Lys
                    755                 760                 765

Ile Thr Cys Glu Cys Thr Lys Pro Asp Ser Tyr Pro Leu Phe Asp Gly
                770                 775                 780

Ile Phe Cys Ser Ser Ser Asn
785                 790
```

<210> SEQ ID NO 11
<211> LENGTH: 710
<212> TYPE: PRT
<213> ORGANISM: Plasmodium falciparum

<400> SEQUENCE: 11

```
Glu Phe Gln Asn Tyr Trp Glu His Pro Tyr Gln Lys Ser Asp Val Tyr
1               5                   10                  15

His Pro Ile Asn Glu His Arg Glu His Pro Lys Glu Tyr Glu Tyr Pro
                20                  25                  30

Leu His Gln Glu His Thr Tyr Gln Gln Glu Asp Ser Gly Glu Asp Glu
                35                  40                  45
```

```
Asn Thr Leu Gln His Ala Tyr Pro Ile Asp His Glu Gly Ala Glu Pro
        50                  55                  60

Ala Pro Gln Glu Gln Asn Leu Phe Ser Ser Ile Glu Ile Val Glu Arg
 65                  70                  75                  80

Ser Asn Tyr Met Gly Asn Pro Trp Thr Glu Tyr Met Ala Lys Tyr Asp
                 85                  90                  95

Ile Glu Glu Val His Gly Ser Gly Ile Arg Val Asp Leu Gly Glu Asp
            100                 105                 110

Ala Glu Val Ala Gly Thr Gln Tyr Arg Leu Pro Ser Gly Lys Cys Pro
            115                 120                 125

Val Phe Gly Lys Gly Ile Ile Ile Glu Asn Ser Lys Thr Thr Phe Leu
130                 135                 140

Thr Pro Val Ala Thr Glu Asn Gln Asp Leu Lys Asp Gly Gly Phe Ala
145                 150                 155                 160

Phe Pro Pro Thr Glu Pro Leu Met Ser Pro Met Thr Leu Asp Asp Met
                165                 170                 175

Arg Asp Leu Tyr Lys Asp Asn Lys Tyr Val Lys Asn Leu Asp Glu Leu
            180                 185                 190

Thr Leu Cys Ser Arg His Ala Gly Asn Met Ile Pro Asp Asn Asp Lys
        195                 200                 205

Asn Ser Asn Tyr Lys Tyr Pro Ala Val Tyr Asp Tyr Glu Asp Lys Lys
210                 215                 220

Cys His Ile Leu Tyr Ile Ala Ala Gln Glu Asn Asn Gly Pro Arg Tyr
225                 230                 235                 240

Cys Asn Lys Asp Gln Ser Lys Arg Asn Ser Met Phe Cys Phe Arg Pro
                245                 250                 255

Ala Lys Asp Ile Ser Phe Gln Asn Tyr Val Tyr Leu Ser Lys Asn Val
            260                 265                 270

Val Asp Asn Trp Glu Lys Val Cys Pro Arg Lys Asn Leu Gln Asn Ala
        275                 280                 285

Lys Phe Gly Leu Trp Val Asp Gly Asn Cys Glu Asp Ile Pro His Val
290                 295                 300

Asn Glu Phe Ser Ala Ile Asp Leu Phe Glu Cys Asn Lys Leu Val Phe
305                 310                 315                 320

Glu Leu Ser Ala Ser Asp Gln Pro Lys Gln Tyr Glu Gln His Leu Thr
                325                 330                 335

Asp Tyr Glu Lys Ile Lys Glu Gly Phe Lys Asn Lys Asn Ala Asp Met
            340                 345                 350

Ile Arg Ser Ala Phe Leu Pro Thr Gly Ala Phe Lys Ala Asp Arg Tyr
        355                 360                 365

Lys Ser His Gly Lys Gly Tyr Asn Trp Gly Asn Tyr Asn Thr Glu Thr
370                 375                 380

Gln Lys Cys Glu Ile Phe Asn Val Lys Pro Thr Cys Leu Ile Asn Asp
385                 390                 395                 400

Lys Ser Tyr Ile Ala Thr Thr Ala Leu Ser His Pro Asn Glu Val Glu
                405                 410                 415

His Asn Phe Pro Cys Ser Leu Tyr Lys Asp Glu Ile Lys Lys Glu Ile
            420                 425                 430

Glu Arg Glu Ser Lys Arg Ile Lys Leu Asn Asp Asn Asp Glu Gly
        435                 440                 445

Asn Lys Lys Ile Ile Ala Pro Arg Ile Phe Ile Ser Asp Asp Ile Asp
450                 455                 460

Ser Leu Lys Cys Pro Cys Ala Pro Glu Ile Val Ser Gln Ser Thr Cys
```

```
                    465                 470                 475                 480
Asn Phe Phe Val Cys Lys Cys Val Glu Lys Arg Ala Glu Val Thr Ser
                485                 490                 495

Asn Asn Glu Val Val Val Lys Glu Glu Tyr Lys Asp Glu Tyr Ala Asp
                500                 505                 510

Ile Pro Glu His Lys Pro Thr Tyr Asp Lys Met Ala Ala Val Thr Val
                515                 520                 525

Asp Thr Val Cys Lys Arg Gly Phe Leu Ile Gln Met Ser Gly His Leu
                530                 535                 540

Glu Cys Lys Cys Glu Asn Asp Leu Val Leu Val Asn Glu Glu Thr Cys
545                 550                 555                 560

Glu Glu Lys Val Leu Lys Cys Asp Glu Lys Thr Val Asn Lys Pro Cys
                565                 570                 575

Gly Asp Phe Ser Lys Cys Ile Lys Ile Asp Gly Asn Pro Val Ser Tyr
                580                 585                 590

Ala Cys Lys Cys Asn Leu Gly Tyr Asp Met Val Asn Asn Val Cys Ile
                595                 600                 605

Pro Asn Glu Cys Lys Asn Val Ala Cys Gly Asn Gly Lys Cys Ile Leu
                610                 615                 620

Asp Thr Ser Asn Pro Val Lys Thr Gly Val Cys Ser Cys Asn Ile Gly
625                 630                 635                 640

Lys Val Pro Asn Val Gln Asp Gln Lys Cys Ser Lys Asp Gly Glu Thr
                645                 650                 655

Lys Cys Ser Leu Lys Cys Leu Lys Glu Asn Glu Ala Cys Lys Ala Val
                660                 665                 670

Asp Gly Ile Tyr Lys Cys Asp Cys Lys Asp Gly Phe Ile Ile Asp Asn
                675                 680                 685

Glu Ala Ser Ile Cys Thr Ser Thr Tyr Gly Lys Ala Ile Ala Val Asp
                690                 695                 700

Ala Phe Ile Lys Lys Ile
705                 710

<210> SEQ ID NO 12
<211> LENGTH: 707
<212> TYPE: PRT
<213> ORGANISM: Plasmodium falciparum

<400> SEQUENCE: 12

Glu Phe Gln Asn Tyr Trp Glu His Pro Tyr Gln Lys Ser Asp Val Tyr
1               5                   10                  15

His Pro Ile Asn Glu His Arg Glu His Pro Lys Glu Tyr Glu Tyr Pro
                20                  25                  30

Leu His Gln Glu His Thr Tyr Gln Gln Glu Asp Ser Gly Glu Asp Glu
                35                  40                  45

Asn Thr Leu Gln His Ala Tyr Pro Ile Asp His Glu Gly Ala Glu Pro
                50                  55                  60

Ala Pro Gln Glu Gln Asn Leu Phe Ser Ser Ile Glu Ile Val Glu Arg
65                  70                  75                  80

Ser Asn Tyr Met Gly Asn Pro Trp Thr Glu Tyr Met Ala Lys Tyr Asp
                85                  90                  95

Ile Glu Glu Val His Gly Ser Gly Ile Arg Val Asp Leu Gly Glu Asp
                100                 105                 110

Ala Glu Val Ala Gly Thr Gln Tyr Arg Leu Pro Ser Gly Lys Cys Pro
                115                 120                 125
```

-continued

```
Val Phe Gly Lys Gly Ile Ile Ile Glu Asn Ser Lys Thr Thr Phe Leu
    130                 135                 140
Thr Pro Val Ala Thr Glu Asn Gln Asp Leu Lys Asp Gly Gly Phe Ala
145                 150                 155                 160
Phe Pro Pro Thr Glu Pro Leu Met Ser Pro Met Thr Leu Asp Asp Met
                165                 170                 175
Arg Asp Leu Tyr Lys Asp Asn Lys Tyr Val Lys Asn Leu Asp Glu Leu
            180                 185                 190
Thr Leu Cys Ser Arg His Ala Gly Asn Met Ile Pro Asp Asn Asp Lys
        195                 200                 205
Asn Ser Asn Tyr Lys Tyr Pro Ala Val Tyr Tyr Glu Asp Lys Lys
    210                 215                 220
Cys His Ile Leu Tyr Ile Ala Ala Gln Glu Asn Asn Gly Pro Arg Tyr
225                 230                 235                 240
Cys Asn Lys Asp Gln Ser Lys Arg Asn Ser Met Phe Cys Phe Arg Pro
                245                 250                 255
Ala Lys Asp Ile Ser Phe Gln Asn Tyr Val Tyr Leu Ser Lys Asn Val
            260                 265                 270
Val Asp Asn Trp Glu Lys Val Cys Pro Arg Lys Asn Leu Gln Asn Ala
        275                 280                 285
Lys Phe Gly Leu Trp Val Asp Gly Asn Cys Glu Asp Ile Pro His Val
    290                 295                 300
Asn Glu Phe Ser Ala Ile Asp Leu Phe Glu Cys Asn Lys Leu Val Phe
305                 310                 315                 320
Glu Leu Ser Ala Ser Asp Gln Pro Lys Gln Tyr Glu Gln His Leu Thr
                325                 330                 335
Asp Tyr Glu Lys Ile Lys Glu Gly Phe Lys Asn Lys Asn Ala Asp Met
            340                 345                 350
Ile Arg Ser Ala Phe Leu Pro Thr Gly Ala Phe Lys Ala Asp Arg Tyr
        355                 360                 365
Lys Ser His Gly Lys Gly Tyr Asn Trp Gly Asn Tyr Asn Thr Glu Thr
    370                 375                 380
Gln Lys Cys Glu Ile Phe Asn Val Lys Pro Thr Cys Leu Ile Asn Asp
385                 390                 395                 400
Lys Ser Tyr Ile Ala Thr Thr Ala Leu Ser His Pro Asn Glu Val Glu
                405                 410                 415
His Asn Phe Pro Cys Ser Leu Tyr Lys Asp Glu Ile Lys Lys Glu Ile
            420                 425                 430
Glu Arg Glu Ser Lys Arg Ile Lys Leu Asn Asp Asn Asp Glu Gly
        435                 440                 445
Asn Lys Lys Ile Ile Ala Pro Arg Ile Phe Ile Ser Asp Asp Ile Asp
    450                 455                 460
Ser Leu Lys Cys Pro Cys Ala Pro Glu Ile Val Ser Gln Ser Thr Cys
465                 470                 475                 480
Asn Phe Phe Val Cys Lys Cys Val Glu Lys Arg Ala Glu Val Thr Ser
                485                 490                 495
Asn Asn Glu Val Val Val Lys Glu Glu Tyr Lys Asp Glu Tyr Ala Asp
            500                 505                 510
Ile Pro Glu His Lys Pro Thr Tyr Asp Lys Met Ala Ala Val Thr Val
        515                 520                 525
Asp Thr Val Cys Lys Arg Gly Phe Leu Ile Gln Met Ser Gly His Leu
    530                 535                 540
Glu Cys Lys Cys Glu Asn Asp Leu Val Leu Val Asn Glu Glu Thr Cys
```

```
545                 550                 555                 560
Glu Glu Lys Val Leu Lys Cys Asp Glu Lys Thr Val Asn Lys Pro Cys
                565                 570                 575

Gly Asp Phe Ser Lys Cys Ile Lys Ile Asp Gly Asn Pro Val Ser Tyr
                580                 585                 590

Ala Cys Lys Cys Asn Leu Gly Tyr Asp Met Val Asn Val Cys Ile
        595                 600                 605

Pro Asn Glu Cys Lys Asn Val Ala Cys Gly Asn Gly Lys Cys Ile Leu
    610                 615                 620

Asp Thr Ser Asn Pro Val Lys Thr Gly Val Cys Ser Cys Asn Ile Gly
625                 630                 635                 640

Lys Val Pro Asn Val Gln Asp Gln Lys Cys Ser Lys Asp Gly Glu Thr
                645                 650                 655

Lys Cys Ser Leu Lys Cys Leu Lys Glu Asn Glu Ala Cys Lys Ala Val
                660                 665                 670

Asp Gly Ile Tyr Lys Cys Asp Cys Lys Asp Gly Phe Ile Ile Asp Asn
        675                 680                 685

Glu Ala Ser Ile Cys Thr Thr Asn Gly Ile Arg Tyr His Tyr Asp Glu
    690                 695                 700

Tyr Ile His
705
```

THREE-COMPONENT-MULTISTAGE MALARIA VACCINE

CROSS REFERENCE TO RELATED APPLICATIONS

This is a US national phase application of international patent application no. PCT/EP2015/070044, filed Sep. 2, 2015, which itself claims priority to European application EP 14183995.1, filed Sep. 8, 2014 and US provisional application no. 62/047,286 filed Sep. 8, 2014. Each of the applications referred to in this paragraph are herein incorporated by reference in their entireties herein.

REFERENCE TO SEQUENCE LISTING SUBMITTED ELECTRONICALLY

The official copy of the sequence listing is submitted electronically via EFS-Web as an ASCII formatted sequence listing with file "PCTEP2015070044 SEQID" created on Mar. 06, 2017, and having a size of 43 Kilobytes. The sequence listing contained in this ASCII formatted document forms part of the specification and is herein incorporated by reference in its entirety.

FIELD OF THE DISCLOSURE

The present disclosure relates to novel malaria vaccines composed of different recombinant proteins, in particular recombinant fusion proteins comprising several different *Plasmodium falciparum* antigens from the pre-erythrocytic, the blood, and the sexual parasite main stages. The proteins may be used in a mixture vaccine formulation to elicit protective immune responses in humans. Nucleic acid molecules encoding said recombinant proteins, vectors and host cells containing the nucleic acids and methods for preparation and producing such proteins are also disclosed, as well as antibodies induced or generated by the use of said malaria vaccines and the use of such antibodies or recombinant derivatives for passive immunotherapy.

BACKGROUND

Malaria is a disease caused by infection with parasites of the phylum *Apicomplexa* protozoan, namely parasites of the genus *Plasmodium*, globally causing more than 200 million new infections and 700 thousand deaths every year. Malaria is especially a serious problem in Africa, where one in every five (20%) childhood deaths is due to the effects of the disease. An African child has on average between 1.6 and 5.4 episodes of malaria fever each year.

Malarial diseases in humans are caused by five species of the *Plasmodium* parasite: *P. falciparum, P. vivax, P. ovale, P. malariae* and *P. knowlesi*, wherein the most prevalent being *Plasmodium falciparum* and *Plasmodium vivax*. Malaria caused by *Plasmodium falciparum* (also called malignantor malaria, falciparum malaria or malaria tropica) is the most dangerous form of malaria, with the highest rates of complications and mortality. Almost all malarial deaths are caused by *P. falciparum*.

Briefly, the plasmodial life cycle (FIG. 1) in man starts with the inoculation of a few sporozoites through the bite of an *Anopheles* mosquito. Within minutes, sporozoites invade the hepatocyte and start their development, multiplying by schizogony (liver stage or pre-erythrocytic stage). After a period of 5-14 days—depending on the plasmodial species—schizonts develop into thousands of merozoites that are freed into the bloodstream and invade the red blood cells (RBCs), initiating the blood stage. In the RBC, each merozoite develops into a trophozoite that matures and divides, generating a schizont that, after fully matured, gives rise to up to 32 merozoites within 42-72 h, depending on the plasmodial species. The merozoites, released into the bloodstream, will invade other RBC, maintaining the cycle. Some merozoites, after invading a RBC, develop into sexual forms—the male or female gametocytes which also enter the bloodstream after maturation and erythrocyte rupture. If a female Anopheles mosquito takes its blood meal and ingests the gametocytes, it will become infected and initiates the sexual stage of the *Plasmodium* life cycle. In the mosquito gut, the male gametocyte fuses with the female gametocyte, forming the ookinete, which binds to and passes through the gut wall, remains attached to its external face and transforms into the oocyst. The oocyst will divide by sporogony, giving rise to thousands of sporozoites that are released in the body cavity of the mosquito and eventually migrate to its salivary gland, where they will maturate, becoming capable of starting a new infection in humans when the mosquito bites the host for a blood meal.

Resistance of *Plasmodium falciparum* to the existing anti-malarial drug chloroquine emerged in the sixties and has been spreading since then. In addition, the malaria parasite has developed resistance to most other anti-malarial drugs over the past decades. This poses a major threat to public health in tropical countries and to travellers. There is every reason to believe that the prevalence and degree of anti-malarial drug resistance will continue to increase. The growing number of insecticide resistant vectors and drug resistant parasites further increases the demand for an effective malaria vaccine. Malaria vaccines are not limited to a single mode of action and hold the potential to dramatically alleviate the burden of malaria.

Some of the difficulties to develop an efficient malaria vaccine result from the multi-stage life cycle of the parasite. Each stage of the parasite development is characterized by different sets of surface antigens, eliciting different types of immune responses. Despite the large variety of displayed surface antigens, the immune response against them is often ineffective. One of the reasons is the extensive sequence polymorphism of plasmodial antigens, which facilitates the immune evasion of the different isolates.

A pre-erythrocytic vaccine would protect against the infectious form (sporozoite) injected by a mosquito and thereby inhibit parasite development in the liver. In a previously unexposed individual, if a few parasites were to escape the immune defences induced by a pre-erythrocytic vaccine, they would eventually enter the blood-stage, multiply within the erythrocytes and establish a full-blown disease.

An erythrocytic or blood-stage vaccine would inhibit the invasion and multiplication of the parasite in the red blood cells, thus preventing (or diminishing) severe disease symptoms during the blood infection. However, it is unlikely to completely interrupt the *Plasmodium* life cycle and prevent transmission of the parasite by this approach.

A sexual-stage vaccine would not protect the person being vaccinated, but instead interrupt the cycle of transmission by inhibiting the development of parasites once they are ingested by the mosquito along with antibodies produced in response to the vaccine. Transmission-blocking vaccines could be involved as part of a multi-faceted strategy directed towards parasite elimination and at the same time towards prevention of parasite resistance to anti pre-erythrocytic or erythrocytic treatment.

The above-mentioned complex multistage life cycle of malaria parasites presents unique challenges for a synergistic vaccine approach. Immunity against malaria parasites is stage dependent and species dependent. Many malaria researchers and textbook descriptions believe and conclude that a single-antigen vaccine representing only one stage of the life cycle will not be sufficient and that a multiantigen, multistage vaccine that targets different, that is at least two, stages of parasite development is necessary to induce effective immunity (Mahajan, Berzofsky et al. 2010). The construction of a multiantigen vaccine (with the aim of covering different parasite stages and increasing the breadth of the vaccine-induced immune responses to try to circumvent potential *Plasmodium falciparum* escape mutants) can be achieved by either genetically linking (full-size) antigens together, by a mixture of recombinant proteins or by synthetic-peptide-based (15-25-mer), chemically synthesized vaccines containing several peptides derived from different parasite proteins and stages.

A single fusion protein approach being comprised of several different antigens or several different alleles of a single antigen (to induce antibodies with synergistic activities against the parasite) is hindered by antigenic diversity and the capacity of *P. falciparum* for immune evasion (Richards, Beeson, 2009). A large number of antigens have been evaluated as potential vaccine candidates, but most clinical trials have not shown significant impact on preventing clinical malaria although some of them have shown to reduce parasite growth. The size of the resulting fusion protein/vaccine candidate is another limiting factor allowing only the combination of a few selected antigens, not excluding that the chosen antigens are not targets of natural immunity and/or exhibit significant genetic polymorphism. Highly variable antigens with multiple alleles are obviously targets of the immune response under natural challenge, and vaccine studies of PfAMA1 and PfMSP2 suggest that allele-specific effects can be achieved (Schwartz, 2012). Currently only combination vaccines (being comprised of PfCSP and PfAMA1) are undergoing clinical trials which target the pre-erythrocytic and asexual blood stage of *P. falciparum* (Schwartz, 2012). A multiantigen vaccine candidate, neither a fusion, nor a combination approach, targeting all three life cycle main stages of *Plasmodium* (including the sexual stage in Anopheles mosquitos and thus blocking parasite transmission) has still not been tested in clinical trials.

Therefore the availability of novel and improved multi-component, multi-stage vaccines against *Plasmodium falciparum* would be highly advantageous.

SUMMARY OF THE INVENTION

The present disclosure relates to combinations of recombinant polypeptides, in particular recombinant fusion proteins suitable as human vaccines against malaria comprising a plurality of antigens or antigen domains derived from proteins preferably, but not necessarily presented on the surface of the *Plasmodium falciparum* parasite during different stages in the life cycle of the parasite.

In a first aspect, the present disclosure pertains to mixtures of recombinant proteins suitable as a human vaccine against the parasite *Plasmodium falciparum* comprising a plurality of antigens derived from *Plasmodium falciparum* surface proteins of the pre-erythrocytic, the blood and the sexual main stage of the parasite life cycle, wherein the mixture comprises a) the pre-erytrocytic antigen TSR-domain of PfCSP, or a variant or fragment thereof;

b) one or more variants or fragments of the blood stage antigen apical membrane antigen (PfAMA1) and the merozoite surface protein PfMsp1-19 or variants or fragments thereof, and peptides derived from PfRh5 or variants thereof;

c) the sexual stage, ookinete antigen Pfs25, or a variant or fragment thereof.

In a further aspect, embodiments of this disclosure relate to antibody compositions comprising different isolated antibodies or fragments thereof binding to the different recombinant proteins in the mixture according to the present disclosure.

In another aspect, embodiments of this disclosure relate to pharmaceutical and/or diagnostic compositions comprising a mixture of recombinant proteins and/or antibodies according to the present disclosure.

In a further aspect, embodiments of this disclosure relate to vaccine compositions for immunizing a mammal, in particular a human, against malaria comprising as an active ingredient a mixture of recombinant proteins according to the present disclosure and a carrier in a physiologically acceptable medium.

In still another aspect, embodiments of this disclosure provide nucleic acids encoding said recombinant fusion proteins comprised in a mixture according to the present disclosure, as well as vectors and host cells containing such nucleic acids.

In other aspects, the disclosure relates to the use of a mixture of recombinant proteins according to the present disclosure in the prevention and/or treatment of *malaria tropica*.

Furthermore, methods of immunizing humans against an *Plasmodium* infection, in particular against *Plasmodium falciparum*, comprising administering an effective amount of recombinant proteins comprised in a mixture of the present disclosure, a composition comprising a mixture of recombinant fusion proteins of the present disclosure or a vaccine composition according to the present disclosure are disclosed.

Before the disclosure is described in detail, it is to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

DETAILED DESCRIPTION OF THE INVENTION

Figure 1:
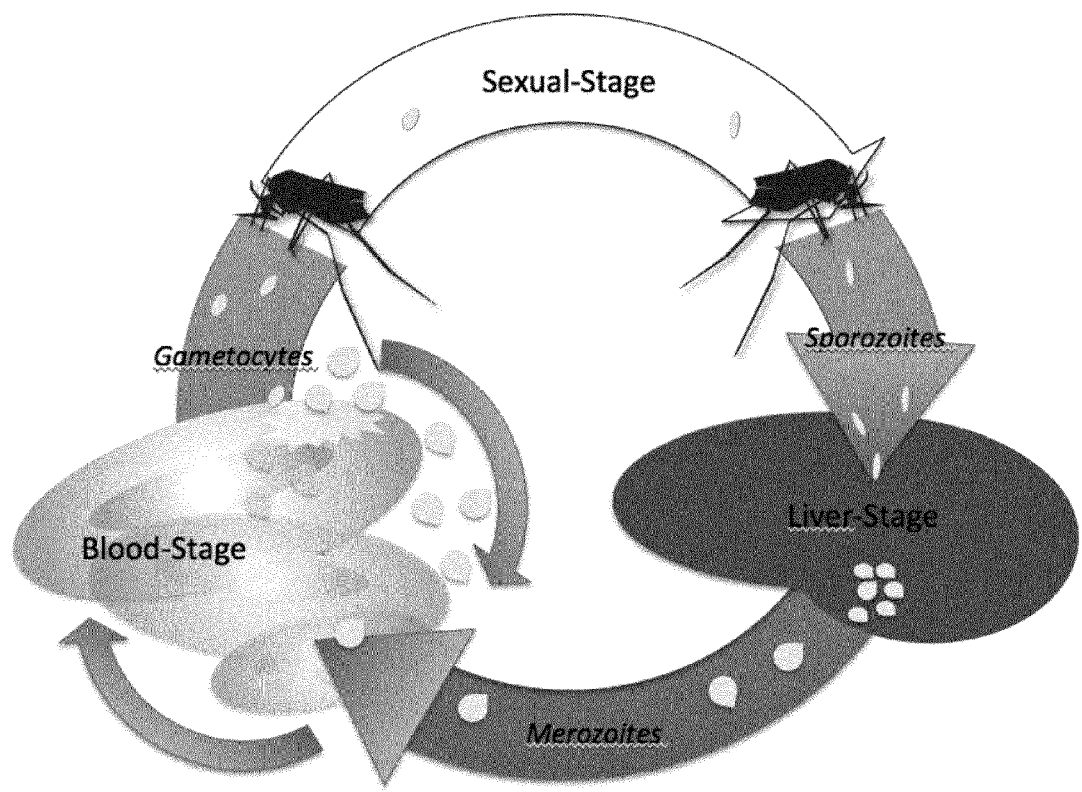
FIG. 1 is a scheme of the life cycle of *Plasmodium falciparum*.

The present disclosure pertains to combinations of recombinant proteins, in particular recombinant fusion proteins suitable as human vaccines against *Plasmodium falciparum*. In advantageous embodiments, the recombinant proteins and vaccine compositions according to the present disclosure combine *Plasmodium falciparum* surface proteins or domains thereof from different stages of the parasite development.

The complex multi-stage life cycle and the genetic variability of *Plasmodium falciparum* represent a significant challenge for successful malaria vaccine development. Depending on the developmental stage the parasite displays different sets of surface proteins that need to be targeted by a protective immune response with the goal to reduce or prevent invasion of liver cells (pre-erythrocytic main stage), reduce or prevent clinical manifestation of malaria (blood main stage) and to reduce or prevent transmission of malaria through the mosquito host. Additionally many important surface proteins are di-, or even polymorphic. Therefore, an efficient, multi-stage malaria vaccine candidate has to combine a plurality of relevant antigens from different stages and cover polymorphisms. One approach to address this is the design of fusion proteins that comprise a number of suitable proteins and/or protein domains. Additionally, the desire for such a vaccine candidate composed of a single polypeptide is mainly driven by practical, technical and economical demands for reproducible, robust and cost-efficient production.

However, to those skilled in the Art, it is also clear, that there is a size limitation for recombinantly expressed fusion proteins. Although protein specific differences have to be taken into account as well, there is a strong decrease of expression levels and yields with increasing length of the polypeptide. Multiple challenges increase over-proportionally with size and the overall properties of large proteins are significantly less amenable to optimization than those of smaller proteins, domains or fragments. All these problems have so far been significant bottlenecks for the development of efficient vaccines against *Plasmodium falciparum* and have resulted in an overwhelming number of sub-optimal vaccine candidates that comprise only multiple linear epitopes, one or two antigens from one or two life cycle main stages. As alternative, chemically or genetically attenuated or inactivated life-vaccines are proposed (e.g. irradiated sporozoites), but such approaches have to deal with difficulties regarding batch-to-batch consistency, scaled-up production and most importantly product safety.

On the other hand using mixtures of recombinant proteins to cover the stages and the antigenic diversity of *Plasmodium falciparum* has several advantages. The use of mixtures of recombinant antigens and/or antigen fusion proteins represent a great option to cover both, the parasite life cycles relevant for spread and clinical manifestation of malaria, as well as the allelic variations of immunologically relevant *Plasmodium falciparum* surface proteins. Allelic variants or even artificial, diversity covering versions can be combined with conserved antigens from different stages by genetic fusion as well as by mixing them in a formulation. Polypeptide size as well as yield and stability in the respective production systems can be considered in the design of suitable fusion proteins in such multicomponent vaccines. On one hand the multicomponent vaccine concept as such has some inherent disadvantages compared to simple subunit vaccine or single fusion protein approaches, caused by increased regulatory issues as well as the need to establish different up-, and downstream processes in the manufacturing, on the other hand the higher efforts are compensated by higher flexibility to match the geographical distribution as well as the evolution of the pathogen, and the broad multi-stage-specific immune response that can be elicited with such antigen cocktails that feature a number of immunorelevant antigens (and their B- and T-cell epitopes) that cannot be easily realized within the context of a single fusion protein.

The recombinant proteins, in particular fusion proteins comprised in the mixtures described in the present disclosure are designed and optimized for optimal yield and stability in the chosen production host *Pichia pastoris*. The fusion proteins have been designed to address distinct stages of the *Plasmodium falciparum* lifecycle and feature the most essential antigens or antigen domains required to elicit the desired immune responses. Combining antigens into fusion proteins is useful to reduce the number of proteins used in a vaccine mixture and reduce upstream, downstream and quality control costs during production, combining stage specific antigens into fusion proteins is a favourable concept to fine-tune the efficacy and the specificity of a multi-stage, multi-component vaccine composition by implementing different ratios of the stage-specific functionalities in the composition.

Importantly, the fusion proteins comprised in the mixtures according to the present disclosure (i) comprise domains derived from different *Plasmodium falciparum* surface proteins and (ii) were designed using building blocks (domains) that have been experimentally identified and verified as well expressing and immunologically relevant.

In summary, the described combinations of the recombinant proteins and fusion proteins of the present disclosure can be well expressed, have a high immunological relevance and have an improved immunogenicity. In advantageous embodiments, the combinations of recombinant proteins and fusion proteins of the present disclosure used as vaccines have the proven ability to elicit protective immunity that blocks infection as well as prevents pathology and interrupts transmission of parasites, and would most likely be a combination vaccine composed of subunits from different parasite stages.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

The phrase "recombinant protein" includes proteins, in particular recombinant fusion proteins that are prepared, expressed, created or isolated by recombinant means, such as proteins expressed using a recombinant expression vector transfected into a host cell.

The term "recombinant fusion protein" refers in particular to a protein produced by recombinant technology which comprises segments i.e. amino acid sequences, from heterologous sources, such as different proteins, different protein domains or different organisms. The segments are joined either directly or indirectly to each other via peptide bonds. By indirect joining it is meant that an intervening amino acid sequence, such as a peptide linker is juxtaposed between segments forming the fusion protein. A recombinant fusion protein is encoded by a nucleotide sequence, which is obtained by genetically joining nucleotide sequences derived from different regions of one gene and/or by joining nucleotide sequences derived from two or more separate genes. These nucleotide sequences can be derived from *P. falciparum*, but they may also be derived from other organisms, the plasmids used for the cloning procedures or from other nucleotide sequences.

Furthermore, the encoding nucleotide sequences may be synthesized in vitro without the need for initial template DNA samples e.g. by oligonucleotide synthesis from digital genetic sequences and subsequent annealing of the resultant fragments. Desired protein sequences can be "reverse translated" e.g. using appropriate software tools. Due to the degeneracy of the universal genetic code, synonymous codons within the open-reading frame (i.e. the recombinant protein coding region) can be exchanged in different ways, e.g. to remove cis-acting instability elements (e.g. AUUUA), to remove, introduce or modify the secondary and tertiary mRNA structures (e.g. pseudoknots, stem-loops, . . . ), to avoid self-complementary regions that might trigger post-transcriptional gene silencing (PGTS), to change the overall AT:GC content, or to adjust the codon-usage to the expression host. Such changes can be designed manually or by using appropriate software tools or through a combination.

A recombinant fusion protein comprising *Plasmodium* surface proteins or domains thereof can be a recombinant product prepared using recombinant DNA methodology and expression in a suitable host cell, as is known in the art (see for example Sambrook et al., (2001) Molecular Cloning, Cold Spring Harbor Laboratory Press, Cold Spring Harbor, N. Y). Nucleotide sequences encoding specific isolated protein domain may be conveniently prepared, for example by polymerase chain reaction using appropriate oligonucleotide primers corresponding to the 5' and 3' regions of the domain required for isolation, and a full length coding of the isolated protein domain sequence as template. The source of the full length coding protein sequence may be for example, DNA extracted from parasite cells or a plasmid vector containing a cloned full length gene. Alternatively, the protein coding sequence may partially or completely be synthesized in vitro or a combination of different approaches may be used. Non-limiting examples of properties of the fusion proteins according to the present are thermostability and pH-stability.

In an advantageous embodiment, the vaccine compositions or mixture of recombinant proteins according to the present disclosure comprise antigens from *Plasmodium falciparum* surface proteins of the pre-erythrocytic, the blood, and the sexual main stage of the parasite life cycle, wherein
  a) the pre-erytrocytic antigen comprises the TSR-domain of PfCSP, or variants or fragments thereof;
  b) the blood stage antigens comprise one or more variants or fragments of apical membrane antigen (PfAMA1) and the merozoite surface protein PfMsp1-19 or variants or fragments thereof and peptides derived from PfRh5 or variants thereof;
  c) the sexual stage antigen(s) comprises the ookinete antigen Pfs25, or variants or fragments thereof.

In a further advantageous embodiment, the vaccine compositions or mixture of recombinant proteins according to the present disclosure comprise antigens derived from *Plasmodium falciparum* surface proteins of the pre-erythrocytic, the blood and the sexual main stage of the parasite life cycle, wherein the mixture comprises
  d) the pre-erytrocytic antigen TSR-domain of PfCSP, or a variant or fragment thereof;
  e) one or more variants or fragments of the blood stage antigen apical membrane antigen (PfAMA1) and the merozoite surface protein PfMsp1-19 or variants or fragments thereof, and peptides derived from PfRh5 or variants thereof;
  f) the sexual stage, ookinete antigen Pfs25, or a variant or fragment thereof.

As used herein the term "antigens derived from *Plasmodium falciparum* surface protein" includes polypeptides comprising the amino acid sequence of the full-length *Plasmodium falciparum* surface protein or in particular only parts of the full-length protein, like specific domains or other parts.

The pre-erytrocytic antigen "PfCSP_TSR" refers to the TSR-domain from Circum Sporozoite Protein (CSP) of *P. falciparum*.

A "TSR domain" is a small about 60-residue domain found in extracellular proteins or in the extracellular part of transmembrane proteins that are involved in immunity, cell adhesion, cell-cell-interactions and neuronal development (Tucker, 2004). Structures of TSR domains from thrombospondin-1 (TSP-1; Tan et al. 2002) and F-spondin (PDB codes 1SZL and 1VEX) have been solved. These show that a TSR domain has an elongated structure consisting of an antiparallel three-stranded β-sheet. The domain core is formed by a stacked array of side chains of conserved tryptophans, arginines, and cysteines. TSRs of several proteins have been reported to mediate glycosaminoglycan (GAG) binding. For example, the plasmodium surface proteins plasmodium CS and TRAP both contain an adhesive thrombospondin type 1 domain, TSR.

The term "fragment" as used herein refers to a continuous part of a natural full-length protein or domain, with or without mutations, which is separate from and not in the context of a full-length *Plasmodium falciparum* surface protein or domain thereof. It may be a structural/topographical or functional subunit of a full length or complete protein.

In one embodiment, the TSR-domain of PfCSP comprises the amino acid sequence of SEQ ID NO. 5.

In another advantageous embodiment, the protein (polypeptide) mixture of the present disclosure comprise one or more variants of the blood stage antigen Apical membrane antigen (PfAMA1) and at least a further *Plasmodium falciparum* blood stage antigen.

As used herein, the antigen "PfAMA1" refers to the *Plasmodium falciparum* Apical membrane antigen (AMA1) extracellular domains 1-3. Recombinant proteins preferably representing the whole ectodomain (Domains I-III) of *Plasmodium falciparum*. AMA-1 can induce antibodies that recognize native parasites and inhibit merozoite invasion of erythrocytes in vitro. The limited polymorphism of PfAMA1 enabled the rational design of three artificial PfAMA1 sequences with a very high coverage of naturally occurring alleles (on average>97%). This Diversity Covering approach (DiCo) is expected to overcome the polymorphism found in nature and to allow a broad response to all naturally occurring AMA1 alleles. (Remarque et al. 2008).

Therefore, the variant of the Apical membrane antigen (PfAMA1) may be any wild type variant of PfAMA1 and/or PfAMA1-DICO1, PfAMA1-DICO2 and/or PfAMA1-DICO3, and also variants thereof, in particular variants with removed or additional potential N-Glycosylation sites. N-linked glycosylation is the attachment of a sugar molecule (a process known as glycosylation) to a nitrogen atom in an amino acid residue in a protein (Drickamer et al. 2006).

In some embodiments of the present disclosure, PfAMA1-DICO1 comprises the amino acid sequence of SEQ ID NO. 1. In further embodiments of the present disclosure, PfAMA1-DICO2 comprises the amino acid sequence of SEQ ID NO. 2. In further embodiments of the present disclosure, PfAMA1-DICO3 comprises the amino acid sequence of SEQ ID NO. 3. In advantageous embodiments, the mixture of recombinant proteins according to the present disclosure comprises the blood stage antigens PfAMA1-DICO1, in particular having the sequence of SEQ ID NO. 1, PfAMA1-DICO2, in particular having the sequence of SEQ ID NO. 2 and PfAMA1-DICO3, in particular having the sequence of SEQ ID NO. 3.

The mixture of recombinant proteins according to the present disclosure comprises further a merozoite surface protein. The several merozoite surface proteins (MSPs) have been identified, but for most of them their function still has to be further elucidated. In the case of the major MSP, named MSP-1, a role has been postulated in merozoite binding to the RBC and in the subsequent biochemical mechanisms involved in invasion. This protein is synthesized as a precursor of 185-210 kDa in the late schizont stage and is processed to generate several polypeptides of varied molecular weights. A 42 kDa polypeptide (MSP1-42) is kept attached to the merozoite membrane, and it is further processed to generate a 19 kDa polypeptide (MSP1-19), which goes into the host cell. In some advantageous embodiments, the further *Plasmodium falciparum* blood stage antigen is PfMsp1-19, in particular comprising the amino acid sequence of SEQ ID NO. 6.

In another embodiments, the mixture of recombinant proteins according to the present disclosure comprises a further *Plasmodium falciparum* blood stage antigen, in particular the blood stage antigen PfRh5, preferably a peptide derived from the blood stage antigen PfRh5 (Douglas et al. 2014) In some advantageous embodiments, the peptide derived from PfRh5 comprises the amino acid sequence SEQ ID NO. 7 and/or SEQ ID NO. 8.

As used herein the term "peptide derived from PfRh5" includes polypeptides comprising only parts of the full-length PfRh5 protein like PfRh5_Q5A and not the entire full-length PfRh5 protein.

In advantageous embodiments, the mixtures according to the present disclosure comprise at least a sexual stage antigen, in particular Pfs25 from *Plasmodium falciparum*, or a variant thereof. Pfs25 is a sexual stage protein which is found on the surface of the parasite zygote as it develops in the mosquito midgut. In some advantageous embodiments, the *Plasmodium falciparum* sexual stage antigen is Pfs25 comprise the amino acid sequence of SEQ ID NO. 4.

In advantageous embodiments, the mixtures according to the present disclosure comprise the polypeptides having the amino acid sequences of SEQ ID NOs. 1 to 7 and/or SEQ ID NOs. 1 to 6 and SEQ ID NO 8 or variants, fragments or homologues polypeptides thereof.

As mentioned above, in some advantageous embodiments, the variants of the antigens in the mixtures like PfCSP_TSR and Pfs25 but also like PfMsp1-19 comprise also removed or additional potential N-Glycosylation sites.

In an advantageous embodiment, some of the *Plasmodium falciparum* antigens are comprised in a recombinant fusion protein, for example the antigens PfAMA1-DICO1, Pfs25 and PfCSP_TSR are comprised in one recombinant fusion protein, the antigens PfAMA1-DICO2, Pfs25 and PfMSP1-19 are comprised in one recombinant fusion protein and/or the antigens PfAMA1-DICO3, Pfs25 and a peptide derived from PfRh5 are comprised in a recombinant fusion protein.

In a further advantageous embodiment, the recombinant fusion protein with PfAMA1-DICO1, Pfs25 and PfCSP_TSR comprises SEQ ID NO. 9, the recombinant fusion protein with PfAMA1-DICO2, Pfs25 and PfMSP1-19 comprises SEQ ID NO. 10, the recombinant fusion protein with PfAMA1-DICO3, Pfs25 and PfRh5_Q5A comprises SEQ ID NO. 11, or the recombinant fusion protein with PfAMA1-DICO3, Pfs25 and PfRh5_9 AD4 comprises SEQ ID NO. 12, or homologous polypeptides thereof, which are produced by recombinant or synthetic methods by substitution, insertion, addition or deletion of one or more amino acid residues.

In an advantageous embodiment, the *Plasmodium falciparum* antigens are comprised in one or more recombinant fusion proteins, for example in a mixture of three recombinant fusion proteins, comprising SEQ ID NO. 9 (Fusion protein 1), SEQ ID NO. 10 (Fusion protein 2) and SEQ ID NO. 11 (Fusion protein 3) a homologous polypeptide thereof, which are produced by recombinant or synthetic methods by substitution, insertion, addition or deletion of one or more amino acid residues.

In another advantageous embodiment, the antigens of the mixture or vaccine compositions according to the present disclosure comprise.

i) PfAMA1-DICO1, Pfs25, and PfCSP_TSR
ii) PfAMA1-DICO2, Pfs25, and PfMsp1-19
iii) PfAMA1-DICO3, Psf25, and PfRh5_Q5A In one embodiment, the PfAMA1-DICO1, the Pfs25, and PfCSP_TSR antigens are comprised in a first recombinant fusion protein, the PfAMA1-DICO2 the Pfs25, and PfMsp1-19 antigens are comprised in a second recombinant fusion protein, and the PfAMA1-DICO3, the Pfs25, and PfRh5_Q5A antigens are comprised in a third recombinant fusion protein.

In another advantageous embodiment, the antigens of the mixture or vaccine compositions according to the present disclosure comprise.
i) PfAMA1-DICO1, Pfs25, and PfCSP_TSR
ii) PfAMA1-DICO2, Pfs25, and PfMsp1-19
iii) PfAMA1-DICO3, Psf25, and PfRh5_9 AD4

In one embodiment, the PfAMA1-DICO1, the Pfs25, and PfCSP_TSR antigens are comprised in a first recombinant fusion protein, the PfAMA1-DICO2 the Pfs25, and PfMsp1-19 antigens are comprised in a second recombinant fusion protein, and the PfAMA1-DICO3, the Pfs25, and PfRh5_9 AD4 antigens are comprised in a third recombinant fusion protein.

In another advantageous embodiment, the vaccine mixtures according to the present disclosure comprise three recombinant fusion proteins, wherein the different recombinant fusion proteins comprises the following antigens:
 a) Fusion protein 1: PfAMA1-DICO1, Pfs25 and PfCSP_TSR
 b) Fusion protein 2: PfAMA1-DICO2, Pfs25 and PfMSP1-19
 c) Fusion protein 3: PfAMA1-DICO3, Pfs25 and PfRh5_Q5A In another advantageous embodiment, the vaccine mixtures according to the present disclosure comprise three recombinant fusion proteins, wherein the different recombinant fusion proteins comprises the following antigens:
 a) Fusion protein 1: PfAMA1-DICO1, Pfs25 and PfCSP_TSR
 b) Fusion protein 2: PfAMA1-DICO2, Pfs25 and PfMSP1-19
 c) Fusion protein 3: PfAMA1-DICO3, Pfs25 and PfRh5_9 AD4

In another embodiment, the above mentioned first recombinant fusion protein (Fusion protein 1) comprises SEQ ID NO. 9, or a homologous polypeptide thereof, which are produced by recombinant or synthetic methods by substitution, insertion, addition or deletion of one or more amino acid residues.

In another embodiment, the above mentioned second recombinant fusion protein (Fusion protein 2) comprises SEQ ID NO. 10, or a homologous polypeptide thereof, which are produced by recombinant or synthetic methods by substitution, insertion, addition or deletion of one or more amino acid residues.

In another embodiment, the above mentioned the third recombinant fusion protein (Fusion protein 3) comprises SEQ ID NO. 11, or a homologous polypeptide thereof, which are produced by recombinant or synthetic methods by substitution, insertion, addition or deletion of one or more amino acid residues.

In another embodiment, the above mentioned the third recombinant fusion protein (Fusion protein 3) comprises SEQ ID NO. 12, or a homologous polypeptide thereof, which are produced by recombinant or synthetic methods by substitution, insertion, addition or deletion of one or more amino acid residues.

In an advantageous embodiment, the mixtures according to the present disclosure comprise three recombinant fusion proteins, wherein the different recombinant fusion proteins having the amino acid sequences of
 a) Fusion protein 1: SEQ ID NO. 9
 b) Fusion protein 2: SEQ ID NO. 10
 c) Fusion protein 3: SEQ ID NO. 11
or homologous polypeptides thereof, which are produced by recombinant or synthetic methods by substitution, insertion, addition or deletion of one or more amino acid residues.

In an another advantageous embodiment, the mixtures according to the present disclosure comprise three recombinant fusion proteins, wherein the different recombinant fusion proteins having the amino acid sequences of
 a) Fusion protein 1: SEQ ID NO. 9
 b) Fusion protein 2: SEQ ID NO. 10
 c) Fusion protein 3: SEQ ID NO. 12
or homologous polypeptides thereof, which are produced by recombinant or synthetic methods by substitution, insertion, addition or deletion of one or more amino acid residues.

For example, the recombinant polypeptides and/or fusion proteins are comprised in the mixture in equimolar or any other ratios. In an advantageous embodiment, the recombinant fusion proteins are comprised in the mixture in equimolar ratios.

Advantageous recombinant proteins, in particular recombinant fusion proteins comprised in the mixture suitable as human vaccines against *Plasmodium falciparum* (SEQ ID NOs: 9 to 12) as well as the individual antigens or antigen domains comprised in the mixtures according to the present disclosure (SEQ ID NOs: 1 to 8) are listed in the following Table 1.

TABLE 1

| SEQ ID | Domain(s) | Sequence |
|---|---|---|
| | Single-stage single or multi-domain proteins for *P. falciparum* vaccines | |
| 1 | PfAMA1-DICO1 | QNYWEHPYQKSDVYHPINEHREHPKEYEYPLHQEHTYQQEDSGED ENTLQHAYPIDHEGAEPAPQEQNLFSSIEIVERSNYMGNPWTEYMA KYDIEEVHGSGIRVDLGEDAEVAGTQYRLPSGKCPVFGKGIIIENSQT TFLTPVATENQDLKDGGFAFPPTKPLMSPMTLDQMRHFYKDNEYV KNLDELTLCSRHAGNMNPDNDKNSNYKYPAVYDDKDKKCHILYIAA QENNGPRYCNKDESKRNSMFCFRPAKDKSFQNYVYLSKNVVDNWE KVCPRKNLENAKFGLWVDGNCEDIPHVNEFSANDLFECNKLVFELS ASDQPKQYEQHLTDYEKIKEGFKNKNADMIRSAFLPTGAFKADRYK SHGKGYNWGNYNRKTQKCEIFNVKPTCLINDKSYIATTALSHPIEVE HNFPCSLYKDEIKKEIERESKRIKLNDNDDEGNKKIIAPRIFISDDKDS LKCPCDPEIVSQSTCNFFVCKCVEKRAEVTSNNEVVVKEEYKDEYAD IPEHKPTYDKM |

TABLE 1-continued

| SEQ ID | Domain(s) | Sequence |
|---|---|---|
| 2 | PfAMA1-DICO2 | QNYWEHPYQKSDVYHPINEHREHPKEYEYPLHQEHTYQQEDSGEDENTLQ HAYPIDHEGAEPAPQEQNLFSSIEIVERSNYMGNPWTEYMAKYDIEEVHGS GIRVDLGEDAEVAGTQYRLPSGKCPVFGKGIIIENSQTTFLKPVATGNQDLK DGGFAFPPTNPLISPMTLNGMRDFYKNNEYVKNLDELTLCSRHAGNMNPD NDENSNYKYPAVYDYNDKKCHILYIAAQENNGPRYCNKDESKRNSMFCFRP AKDKLFENYVYLSKNVVHNWEEVCPRKNLENAKFGLWVDGNCEDIPHVN EFSANDLFECNKLVFELSASDQPKQYEQHLTDYEKIKEGFKNKNADMIRSA FLPTGAFKADRYKSRGKGYNWGNYNRKTQKCEIFNVKPTCLINDKSYIATT ALSHPIEVENNFPCSLYKNEIMKEIERESKRIKLNDNDDEGNKKIIAPRIFISD DKDSLKCPCDPEMVSQSTCRFFVCKCVERRAEVTSNNEVVVKEEYKDEYAD IPEHKPTYDNM |
| 3 | PfAMA1-DICO3 | QNYWEHPYQKSDVYHPINEHREHPKEYEYPLHQEHTYQQEDSGEDENTLQ HAYPIDHEGAEPAPQEQNLFSSIEIVERSNYMGNPWTEYMAKYDIEEVHGS GIRVDLGEDAEVAGTQYRLPSGKCPVFGKGIIIENSKTTFLTPVATENQDLKD GGFAFPPTEPLMSPMTLDDMRDLYKDNKYVKNLDELTLCSRHAGNMIPDN DKNSNYKYPAVYDYEDKKCHILYIAAQENNGPRYCNKDQSKRNSMFCFRPA KDISFQNYVYLSKNVVDNWEKVCPRKNLQNAKFGLWVDGNCEDIPHVNEF SAIDLFECNKLVFELSASDQPKQYEQHLTDYEKIKEGFKNKNADMIRSAFLP TGAFKADRYKSHGKGYNWGNYNTETQKCEIFNVKPTCLINDKSYIATTALS HPNEVEHNFPCSLYKDEIKKEIERESKRIKLNDNDDEGNKKIIAPRIFISDDID SLKCPCAPEIVSQSTCNFFVCKCVEKRAEVTSNNEVVVKEEYKDEYADIPEH KPTYDKM |
| 4 | Pfs25 | VTVDTVCKRGFLIQMSGHLECKCENDLVLVNEETCEEKVLKCDEKTVNKPC GDFSKCIKIDGNPVSYACKCNLGYDMVNNVCIPNECKNVACGNGKCILDTSN PVKTGVCSCNIGINPNVQDQKCSKDGETKCSLKCLKENEACKAVDGIYKCD CKDGFIIDNEASICT |
| 5 | PfCSP-TSR | PSDKHIKEYLNKIQNSLSTEWSPCSVTCGNGIQVRIKPGSANKPKDEL DYANDIEKKICKMEKCSSVFNVVNS |
| 6 | PfMsp1-19 | ISQHQCVKKQCPENSGCFRHLDEREECKCLLNYKQEGDKCVENPNPACNEN NGGCDADAKCTEEDSGSNGKKITCECTKPDSYPLFDGIFCSSSN |
| 7 | PfRH5Peptide_Q5A | STYGKAIAVDAFIKKI |
| 8 | PfRH5Peptide_9AD4 | TNGIRYHYDEYIH |
| 9 | PfAMA1-DICO1_Pfs25_PfCSP-TSR | EFQNYVVEHPYQKSDVYHPINEHREHPKEYEYPLHQEHTYQQEDSG EDENTLQHAYPIDHEGAEPAPQEQNLFSSIEIVERSNYMGNPWTEY MAKYDIEEVHGSGIRVDLGEDAEVAGTQYRLPSGKCPVFGKGIIIENS QTTFLTPVATENQDLKDGGFAFPPTKPLMSPMTLDQMRHFYKDNE YVKNLDELTLCSRHAGNMNPDNDKNSNYKYPAVYDDKDKKCHILYI AAQENNGPRYCNKDESKRNSMFCFRPAKDKSFQNYVYLSKNVVDN WEKVCPRKNLENAKFGLWVDGNCEDIPHVNEFSANDLFECNKLVF ELSASDQPKQYEQHLTDYEKIKEGFKNKNADMIRSAFLPTGAFKAD RYKSHGKGYNWGNYNRKTQKCEIFNVKPTCLINDKSYIATTALSHPI EVEHNFPCSLYKDEIKKEIERESKRIKLNDNDDEGNKKIIAPRIFISDD KDSLKCPCDPEIVSQSTCNFFVCKCVEKRAEVTSNNEVVVKEEYKDE YADIPEHKPTYDKMAAVTVDTVCKRGFLIQMSGHLECKCENDLVLV NEETCEEKVLKCDEKTVNKPCGDFSKCIKIDGNPVSYACKCNLGYDM VNNVCIPNECKNVACGNGKCILDTSNPVKTGVCSCNIGKVPNVQDQ KCSKDGETKCSLKCLKENEACKAVDGIYKCDCKDGFIIDNEASICTAA PSDKHIKEYLNKIQNSLSTEWSPCSVTCGNGIQVRIKPGSANKPKDEL DYANDIEKKICKMEKCSSVFNVVNS |
| 10 | PfAMA1-DICO2_Pfs25_PfMsp1-19 | EFQNYWEHPYQKSDVYHPINEHREHPKEYEYPLHQEHTYQQEDSGEDENT LQHAYPIDHEGAEPAPQEQNLFSSIEIVERSNYMGNPWTEYMAKYDIEEVH GSGIRVDLGEDAEVAGTQYRLPSGKCPVFGKGIIIENSQTTFLKPVATGNQDL KDGGFAFPPTNPLISPMTLNGMRDFYKNNEYVKNLDELTLCSRHAGNMNP DNDENSNYKYPAVYDYNDKKCHILYIAAQENNGPRYCNKDESKRNSMFCF RPAKDKLFENYVYLSKNVVHNWEEVCPRKNLENAKFGLWVDGNCEDIPH VNEFSANDLFECNKLVFELSASDQPKQYEQHLTDYEKIKEGFKNKNADMIR SAFLPTGAFKADRYKSRGKGYNWGNYNRKTQKCEIFNVKPTCLINDKSYIA TTALSHPIEVENNFPCSLYKNEIMKEIERESKRIKLNDNDDEGNKKIIAPRIFI SDDKDSLKCPCDPEMVSQSTCRFFVCKCVERRAEVTSNNEVVVKEEYKDEY ADIPEHKPTYDNMAAVTVDTVCKRGFLIQMSGHLECKCENDLVLVNEETCE EKVLKCDEKTVNKPCGDFSKCIKIDGNPVSYACKCNLGYDMVNNVCIPNEC KNVACGNGKCILDTSNPVKTGVCSCNIGKVPNVQDQKCSKDGETKCSLKCL KENEACKAVDGIYKCDCKDGFIIDNEASICTAAISQHQCVKKQCPENSGCFR HLDEREECKCLLNYKQEGDKCVENPNPACNENNGGCDADAKCTEEDSGSN GKKITCECTKPDSYPLFDGIFCSSSN |
| 11 | PfAMA1-DICO3_Pfs25_PfRh5_Q5A | EFQNYVVEHPYQKSDVYHPINEHREHPKEYEYPLHQEHTYQQEDSGEDENT LQHAYPIDHEGAEPAPQEQNLFSSIEIVERSNYMGNPWTEYMAKYDIEEVH GSGIRVDLGEDAEVAGTQYRLPSGKCPVFGKGIIIENSKTTFLTPVATENQDL KDGGFAFPPTEPLMSPMTLDDMRDLYKDNKYVKNLDELTLCSRHAGNMIP |

TABLE 1-continued

| SEQ ID | Domain(s) | Sequence |
|---|---|---|
| | | DNDKNSNYKYPAVYDYEDKKCHILYIAAQENNGPRYCNKDQSKRNSMFCF<br>RPAKDISFQNYVYLSKNVVDNWEKVCPRKNLQNAKFGLWVDGNCEDIPHV<br>NEFSAIDLFECNKLVFELSASDQPKQYEQHLTDYEKIKEGFKNKNADMIRSA<br>FLPTGAFKADRYKSHGKGYNWGNYNTETQKCEIFNVKPTCLINDKSYIATT<br>ALSHPNEVEHNFPCSLYKDEIKKEIERESKRIKLNDNDDEGNKKIIAPRIFISD<br>DIDSLKCPCAPEIVSQSTCNFFVCKCVEKRAEVTSNNEVVVKEEYKDEYADI<br>PEHKPTYDKMAAVTVDTVCKRGFLIQMSGHLECKCENDLVLVNEETCEEK<br>VLKCDEKTVNKPCGDFSKCIKIDGNPVSYACKCNLGYDMVNNVCIPNECKN<br>VACGNGKCILDTSNPVKTGVCSCNIGKVPNVQDQKCSKDGETKCSLKCLKE<br>NEACKAVDGIYKCDCKDGFIIDNEASICTSTYGKAIAVDAFIKKI |
| 12 | PfAMA1-<br>DICO3_Pfs25_PfRh5_9AD4 | EFQNYVVEHPYQKSDVYHPINEHREHPKEYEYPLHQEHTYQQEDSGEDENT<br>LQHAYPIDHEGAEPAPQEQNLFSSIEIVERSNYMGNPWTEYMAKYDIEEVH<br>GSGIRVDLGEDAEVAGTQYRLPSGKCPVFGKGIIIENSKTTFLTPVATENQDL<br>KDGGFAFPPTEPLMSPMTLDDMRDLYKDNKYVKNLDELTLCSRHAGNMIP<br>DNDKNSNYKYPAVYDYEDKKCHILYIAAQENNGPRYCNKDQSKRNSMFCF<br>RPAKDISFQNYVYLSKNVVDNWEKVCPRKNLQNAKFGLWVDGNCEDIPHV<br>NEFSAIDLFECNKLVFELSASDQPKQYEQHLTDYEKIKEGFKNKNADMIRSA<br>FLPTGAFKADRYKSHGKGYNWGNYNTETQKCEIFNVKPTCLINDKSYIATT<br>ALSHPNEVEHNFPCSLYKDEIKKEIERESKRIKLNDNDDEGNKKIIAPRIFISD<br>DIDSLKCPCAPEIVSQSTCNFFVCKCVEKRAEVTSNNEVVVKEEYKDEYADI<br>PEHKPTYDKMAAVTVDTVCKRGFLIQMSGHLECKCENDLVLVNEETCEEK<br>VLKCDEKTVNKPCGDFSKCIKIDGNPVSYACKCNLGYDMVNNVCIPNECKN<br>VACGNGKCILDTSNPVKTGVCSCNIGKVPNVQDQKCSKDGETKCSLKCLKE<br>NEACKAVDGIYKCDCKDGFIIDNEASICTTNGIRYHYDEYIH |

Further embodiments relates to methods for conjugating the recombinant protein to itself or to other molecules, proteins or carriers, in particular by random ways or by using site-directed coupling methods. In particular, site directed coupling can be accommodated to N-glycosylation site specifically retained within or introduced into the recombinant protein.

It is also understood that the present disclosure comprises all molecules that are derived from the polynucleotides of the disclosure and all variants thereof described in this application, by posttranslational processing compared to the genetically encoded amino acid sequence. These posttranslational modifications comprise, but are not limited to, proteolytic cleavage of N-terminal sequences such as leader and/or pro-sequences, proteolytic removal of C-terminal extensions, N- and/or O-glycosylation or de-glycosylation, lipidation, acylation, deamidation, pyroglutamate formation, phosphorylation and/or others, or any combination thereof, as they occur during production/expression by the native host or any suitable expression host. These post-translational modifications may or may not have an influence on the properties of the proteins as explored herein.

The term "modification" as used herein, refers for example to substitutions, insertions or deletions of amino acid residues at specific positions in an amino acid sequence as well as the phosphorylation, acetylation like palmitoylation, methylation, sulphation, glycosylation, lipidation like isoprenylation, farnesylation, attachment of a fatty acid moiety, glypiation and/or ubiquitinylation of specific positions on the polypeptide, or combinations thereof.

The term "modifying", as used herein, includes changing one or more amino acids in the antibodies or antigen-binding portions thereof. The change can be produced by adding, substituting or deleting an amino acid at one or more positions. The change can be produced using known techniques, such as PCR mutagenesis.

The term "variant" includes a homologous polypeptide to the original non-variant polypeptide and could be recognized by at least one antibody binding to the original non-variant polypeptide, wherein the variant comprises an alteration, i.e., a substitution, insertion, and/or deletion, at one or more (several) positions. The term "variant" includes also polypeptides having modifications but comprises the same or a homologues amino acid sequence of the original polypeptide.

The term "homologous polypeptide" according to the present disclosure comprises any recombinant protein with a sequence identity of at least 70% or preferably at least 80%, 85%, 90%, 95%, 97% or 99% to the recombinant proteins in the mixtures or vaccine compositions according to the present disclosure. In particular to the mixtures comprising the sequences of SEQ ID NO. 9, SEQ ID NO. 10 and SEQ ID NO. 11 or SEQ ID NO. 12.

Homology is defined as an analogue or variant of the fusion protein of the present disclosure. The fusion protein is characterised by specific amino acids and is encoded by specific nucleic acid sequences. It will be understood that such sequences include analogues and variants produced by recombinant or synthetic methods wherein such polypeptide sequences have been modified by substitution, insertion, addition or deletion of one or more amino acid residues in the recombinant polypeptide and still be immunogenic in any of the biological assays described herein. Substitutions are preferably "conservative". Substitutions are preferably silent substitutions in the codon usage which will not lead to any change in the amino acid sequence, but may be introduced to enhance the expression of the protein. According to Table 4 amino acids in the same block of the second column and preferably in the same line of the fourth column may be substituted for each other. The amino acids in the second and fourth column are indicated in one-letter code.

In another aspect, the present disclosure pertains to an isolated nucleic acid molecule or a plurality of nucleic acid molecules encoding
   a) a nucleic acid molecule encoding the polypeptides having the sequence of SEQ ID NO. 9, SEQ ID NO. 10, SEQ ID NO. 11 or SEQ ID NO. 12.
   b) a nucleic acid molecule encoding for a modified form of the sequences having the sequence of SEQ ID NO. 9, SEQ ID NO. 10, SEQ ID NO. 11 or SEQ ID NO. 12, preferably in which one or more amino acid residues are conservatively substituted;

c) a nucleic acid molecule that is capable of hybridizing to any of the nucleic acid molecules of a)-b) under stringent conditions
d) a nucleic acid molecule that is capable of hybridizing to the complement of any of the nucleic acid molecules of a)-c) under stringent conditions
e) a nucleic acid molecule having a sequence identity of of at least 80%, at least 85%, at least 90% or at least 95% with any of the nucleic acid molecules of a)-d),
f) or a complement of any of the nucleic acid molecules of a)-e).

The term "nucleic acid molecule" or "nucleic acid" is intended to indicate any single- or double stranded nucleic acid molecule of cDNA, genomic DNA, synthetic DNA or RNA, Peptide nucleic acid (PNA) or LNA origin.

The terms "conservative mutation", or "conservative substitution", respectively, refer to an amino acid mutation that a person skilled in the art would consider a conservative to a first mutation. "Conservative" in this context means a similar amino acid in terms of the amino acid characteristics. If, for example, a mutation leads at a specific position to a substitution of a non-aliphatic amino acid residue (e.g. Ser) with an aliphatic amino acid residue (e.g. Leu) then a substitution at the same position with a different aliphatic amino acid (e.g. Ile or Val) is referred to as a conservative mutation. Further amino acid characteristics include size of the residue, hydrophobicity, polarity, charge, pK-value, and other amino acid characteristics known in the art. Accordingly, a conservative mutation may include substitution such as basic for basic, acidic for acidic, polar for polar etc. The sets of amino acids thus derived are likely to be conserved for structural reasons.

The present disclosure is also directed to vectors comprising a nucleotide molecule of the present disclosure. The term "vector" includes a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

In advantageous embodiments, the nucleic sequences of the recombinant proteins can be inserted into a suitable yeast expression vector which can be transformed for example into *Pichia pastoris*.

The present disclosure is also directed to host cell with a vector comprising the recombinant fusion proteins according to the present disclosure. The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Host cells include progeny of a single host cell, and the progeny may not necessarily be completely identical (in morphology or in total DNA complement) to the original parent cell due to natural, accidental, or deliberate mutation and/or change. A host cell includes a cell transfected or infected in vivo or in vitro with a recombinant vector or a polynucleotide of the present disclosure. A host cell which comprises a recombinant vector of the invention may also be referred to as a "recombinant host cell".

The term "host cell(s)" refers to cell(s) which may be used in a process for purifying a recombinant protein in accordance with the present disclosure. Such host cells carry the protein of interest (POI). A host cell may also be referred to as a protein-expressing cell. A host cell, according to the present invention, may be, but is not limited to, prokaryotic cells, eukaryotic cells, archeobacteria, bacterial cells, insect cells, yeast, mammal cells, and/or plant cells. Bacteria envisioned as host cells can be either gram-negative or gram-positive, e.g. *Escherichia coli, Erwinia* sp., *Klebsellia* sp., *Lactobacillus* sp., *Pseudomonas fluorescence* sp. or *Bacillus subtilis*. Typical yeast host cells are selected from the group consisting of *Saccharomyces cerevisiae*, and *Pichia pastoris*.

In advantageous embodiments, the host cell is a yeast cell, in particular a *Pichia pastoris* yeast cell.

To express a recombinant protein according to the present disclosure, a DNA encoding the fusion protein or parts thereof, may be inserted into an expression vector such that the gene is operably linked to transcriptional and translational control sequences. In this context, the term "operably linked" means that a protein gene is ligated into a vector such that transcriptional and translational control sequences within the vector serve their intended function of regulating the transcription and translation of the protein gene. The expression vector and expression control sequences are chosen to be compatible with the expression host cell used. The isolated protein domain sequences are typically inserted into the same expression vector. The protein genes are inserted into the expression vector by standard methods. Additionally, the recombinant expression vector can encode a signal peptide that facilitates secretion of the target protein into the culture supernatant.

In general, those skilled in the art are well able to construct vectors and design protocols for recombinant gene expression. For further details see, for example, Molecular Cloning: a Laboratory Manual: 2nd edition, Sambrook et al, 1989, Cold Spring Harbor Laboratory Press (or later editions of this work) and Current Protocols in Molecular Biology, Second Edition, Ausubel et al. eds., John Wiley & Sons, 1992, which are incorporated herein by reference.

In an advantageous embodiment, the expression vectors may be delivered to yeast cells according to known techniques.

Further aspects of the disclosure relate to: a method of expressing in a host cell a recombinant protein as described herein from a nucleic acid molecule described herein; a host cell capable of expressing a fusion protein as described herein in appropriate culture conditions for producing said protein; a method of producing a recombinant protein comprising culturing such a host cell under appropriate conditions, which method may further comprise isolating said protein from the cell culture, and which method may further comprise admixing the isolated fusion protein with a suitable further component (which may, for example, be another protein or an excipient or carrier).

As discussed above, in accordance with the present disclosure, the recombinant proteins may be produced in any desirable system. Vector constructs and expression systems are well known in the art and may be adapted to incorporate use of recombinant fusion polypeptides provided herein.

In general, standard methods known in the art may be used for culturing yeasts in accordance with the disclosure.

In a certain embodiments, recombinant polypeptides/proteins in accordance with the present description may be produced by any known method. In some embodiments, a fusion protein is expressed in a yeast cell or portion thereof. Proteins may be isolated and purified in accordance with conventional conditions and techniques known in the art. These include methods such as extraction, precipitation, chromatography, affinity chromatography, electrophoresis, and the like. The present invention involves purification and affordable scaling up of production of recombinant polypeptide(s) using any of a variety of plant expression systems known in the art and provided herein.

Therefore, some advantageous embodiments pertain to methods of producing the recombinant proteins, in particular the recombinant fusion proteins of the present disclosure, wherein the methods comprise the steps of:
  a) providing a nucleic acid construct comprising a nucleic acid encoding the recombinant fusion protein,
  b) introducing the nucleic acid construct into a host cell, and
  c) maintaining the host cell under conditions permitting expression of the fusion protein, Furthermore, the disclosure pertains to a vaccine composition for immunizing human individuals against *Plasmodium falciparum* comprising as an active ingredient a mixture according to the present disclosure and a carrier in a physiologically acceptable medium.

A "vaccine" is for example a composition of matter molecules that, when administered to a subject, induces an immune response. Vaccines can comprise polynucleotide molecules, polypeptide molecules, and carbohydrate molecules, as well as derivatives and combinations of each, such as glycoproteins, lipoproteins, carbohydrate-protein conjugates, fusions between two or more polypeptides or polynucleotides, and the like. A vaccine may further comprise a diluent, an adjuvant, a carrier, or combinations thereof, as would be readily understood by those in the art. In one embodiment, the vaccine the composition comprises further an adjuvant.

As mentioned above, the recombinant proteins in the vaccine composition may be coupled to a carbohydrate or a lipid moiety, e.g. a carrier, or a modified in other ways, e.g. being acetylated. Suitable carriers are selected from the group consisting of a polymer to which the polypeptide(s) is/are bound by hydrophobic non-covalent interaction, such as a plastic, e.g. polystyrene, or a polymer to which the polypeptide(s) is/are covalently bound, such as a polysaccharide, or a polypeptide, e.g. bovine serum albumin, ovalbumin or keyhole limpet haemocyanin. Suitable vehicles are selected from the group consisting of a diluent and a suspending agent. The adjuvant is preferably selected from the group consisting of dimethyldioctadecylammonium bromide (DDA), Quil A, poly I:C, aluminium hydroxide, Freund's incomplete adjuvant, IFN-gamma, IL-2, IL-12, monophosphoryl lipid A (MPL), Treholose Dimycolate (TDM), Trehalose Dibehenate and muramyl dipeptide (MDP), Inuline, or Glucopyranosyl lipid adjuvant-stable emulsion (GLA-SE).

Preparation of vaccines which contain peptide sequences as active ingredients is generally well understood in the art, as exemplified by U.S. Pat. Nos. 4,608,251; 4,601,903; 4,599,231 and 4,599,230, all incorporated herein by reference.

Other methods of achieving adjuvant effect for the vaccine include use of agents such as aluminum hydroxide or phosphate (alum), synthetic polymers of sugars (Carbopol), aggregation of the protein in the vaccine by heat treatment, aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20% solution of a perfluorocarbon (Fluosol-DA) used as a block substitute may also be employed. Other possibilities involve the use of immune modulating substances such as cytokines or synthetic IFN-gamma inducers such as poly I:C in combination with the above-mentioned adjuvants.

Another possibility for achieving adjuvant effect is to employ the technique described in Gosselin et al, 1992. In brief, a relevant antigen such as an antigen of the present invention can be conjugated to an antibody (or antigen binding antibody fragment) against the Fc-receptors on monocytes/macrophages.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 micro g to 1000 micro g, such as in the range from about 1 micro g to 300 micro g, and especially in the range from about 10 micro g to 50 micro g. Suitable regimens for initial administration and booster shots are also variable but are typified by an initial administration followed by subsequent inoculations or other administrations. The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5 percent to 10 percent, preferably 1-2 percent. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10-95 percent of active ingredient, preferably 25-70%.

In many instances, it will be necessary to have multiple administrations of the vaccine. Especially, vaccines can be administered to prevent an infection with malaria and/or to treat established malarial infection. When administered to prevent an infection, the vaccine is given prophylactically, before definitive clinical signs or symptoms of an infection are present.

Due to genetic variation, different individuals may react with immune responses of varying strength to the same protein. Therefore, the vaccine according to the disclosure may comprise several different fusion proteins according to the present disclosure in order to increase the immune response. The vaccine may comprise two or more fusion proteins or immunogenic portions, where all of the proteins are as defined above, or some but not all of the peptides may be derived from P. falciparum or other parasites from the genus Plasmodium, in the latter example, the polypeptides not necessarily fulfilling the criteria set forth above for polypeptides may either act due to their own immunogenicity or merely act as adjuvants. The vaccine may comprise 1-20, such as 2-20 or even 3-20 different recombinant proteins or fusion proteins, such as 3-10 different proteins or fusion proteins.

In some embodiments, the fusion protein is adsorbed on or covalently bound to said carrier. In another embodiment, the carrier is a carrier protein.

The disclosure pertains also to antibody compositions comprising isolated antibodies or fragments thereof binding to the different recombinant proteins in the mixture according to the present disclosure. According to the present disclosure, the term "antibody" includes, but is not limited to recombinant antibodies, polyclonal antibodies, monoclonal antibodies, single chain antibodies, humanized antibodies, minibodies, diabodies, nanobodies, tribodies as well as antibody fragments, including antigen-binding portion of the antibodies according to the present disclosure, such as Fab', Fab, F(ab')$_2$ and single domain antibodies as mentioned above.

A further aspect of the present disclosure pertains to methods for treating and/or preventing malaria caused by Plasmodium falciparum in a patient, which comprises administering a therapeutically effective amount of a mixture of recombinant proteins according to the present disclosure.

The actual dosage amount of a mixture of the present disclosure administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

The following methods and examples are offered for illustrative purposes only, and are not intended to limit the scope of the present disclosure in any way.
Methods and Examples In the following example materials and methods of the present disclosure are provided. It should be understood that these examples are for illustrative purpose only and are not to be construed as limiting this disclosure in any manner. All publications, patents, and patent applications cited herein are hereby incorporated by reference in their entirety for all purposes.

As example three different recombinant fusion proteins named VAMAX I (SEQ ID NO. 9). VAMAX II (SEQ ID NO. 10) and VAMAX VI (SEQ ID NO. 11) were produced in P.pastoris by fermentation. Afterwards the proteins were purified and analysed by SDS-PAGE and Western Blot.

1. Cloning of Expression Constructs

Synthetic genes (GeneArt) optimized for P. pastoris. codon usage were inserted into a P. pastoris expression vector comprising the methanol inducible AOX1 promotor and AOX1 terminator to control transgene expression. The expression cassette also featured the native S.cerevisiae alpha-factor secretion sequence. An pUC origin of replication, and for selection the Zeocin resistance protein Sh ble under the control of the S.cerevisiae TEF1 and the synthetic, procaryotic EM7 as promotors and the S.cerevisiae CYC1 region as terminator. The optimized sequences were inserted into the P.pastoris expression vector as EcoRI and XbaI fragments. 1.5 μg aliquots of each plasmid were linearized with PmeI (NEB, Frankfurt, Germany), purified by precipitation (70% isopropanol, 10% 4 M LiCl), and redissolved in 10 μl sterile ddH2O. P. pastoris KM71H cells were prepared for electroporation as described by (Cregg et al. 2000) and stored at −80° C. Electroporation was carried out by introducing 5 μl of plasmid DNA into 40 μl of competent cells using a Multiporator device (Eppendorf, Wesseling-Berzdorf, Germany) with 2-mm cuvettes, a charging voltage of 2500 V, and a pulse length of 5 ms. The cells were immediately mixed with ice-cold 1 M sorbitol and transferred in 2 ml of YSD medium (1% yeast extract, 2% soya peptone, 2% dextrose). After incubation at 28° C. and 160 rpm (VKS-75 Control Shaker, Edmund Bühler, Hechingen, Germany) for 45 min, the cells were pelleted by centrifugation (800×g), resuspended in 50 μl sterile water, plated on selective medium (YSD supplemented with 100 μg/L Zeocin), and placed at 28° C. in the dark for 48 h.

Figure 2:
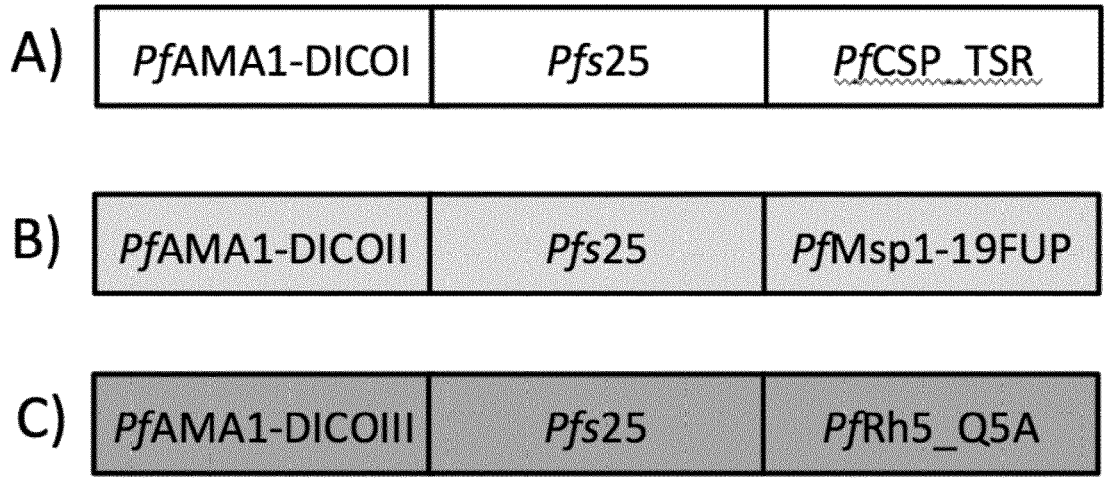
FIG. 2 shows an embodiment of a vaccine mixture containing a first recombinant fusion protein comprising the antigens PfAMA1-DICO1, Pfs25 and PfCSP_TSR (A), a second recombinant fusion protein comprising the antigens PfAMA1-DICO2, Pfs25 and PfMSP1-19 (B), and a third recombinant fusion protein comprising the antigens PfAMA1-DICO3, Pfs25 and PfRh5_Q5A.

FIG. 2 shows a schematic representation of the recombinant fusion proteins named VAMAX I (SEQ ID NO. 9). VAMAX II (SEQ ID NO. 10) and VAMAX VI (SEQ ID NO. 11) used in this example.

2. Screening

Up to 24 colonies of each transformation event were picked in 100 μl of YSD selection medium in microtiter plates and incubated at 28° C. for 24 h in a VKS-75 Control Shaker (Edmund Bühler, Hechingen, Germany). 50 μl precultures were used to inoculate 750 μl YSG medium (1% yeast extract, soya peptone 2%, glycerol 2%) supplemented with Zeocin in deep-well plates. After incubation for 24 h at 28° C. and 900 rpm (VKS-75 Control Shaker, Edmund Bühler, Hechingen, Germany), expression was induced twice by the addition of 1% methanol at 24-h intervals. Cells were harvested by centrifugation (2000×g, 4° C., 10 min) and the supernatant was tested for the presence of the secreted recombinant protein by dot-blot using Pfs25-specific murine monoclonal antibody mAb 4B7 produced from the corresponding myeloma cell line MRA-315 (obtained through the MR4, deposited by L H Miller and A Saul) at a dilution of 1/5000 followed by detection with was Goat anti-mouse H+L alkaline phosphatase labeled. Bands were visualized with NBT/BCIP (1 mg·ml-1 in substrate buffer: 150 mM NaCl, 2 mM MgCl2, 50 mM Tris-HCl, pH 9.6). Between the incubation steps the membranes were washed three times with PBS supplemented with 0.05% (v/v) Tween-20.

3. Fed-Batch Fermentation

Inoculum Preparation

The inoculum was prepared by transferring 150 µL of a previously established research cell bank to a 500 ml bottom-baffled shake flask containing 200 ml YSG. The culture was incubated overnight at 28° C. and a shaking speed of 160 rpm.

Fermentation

Cultivation was carried out in a BioPilot 40 bioreactor (Applikon, Schiedam, The Netherlands) with a working volume of 30 L and a H/D ratio of 3. The reactor was equipped with three six-blade Rushton impellers, one L-sparger to ensure high gas flow rates rates, a BlueInOne Ferm off-gas analyzer (BlueSens, Herten, Germany), and an ALCOSENS probe in combination with an ACTOMAT N II control system (Heinrich Frings, Bonn, Germany).

Fed-batch cultivation was initiated with 15 L reduced basal salts medium, containing 25 ml/L $H_3PO_4$ (85%, v/v), 2.31 g/L $MgSO_4$.7 $H_2O$, 0.18 g/L $CaSO_4$.2 $H_2O$, 0.72 g/L KOH, 2.85 g/L $K_2SO_4$, 20 g/L glycerol, and 0.25 ml/L Struktol J673 (Schill+Seilacher "Struktol" GmbH, Hamburg, Germany) to prevent foaming.

After sterilization and pH adjustment with 25% (w/w) ammonia, 8 ml/L of *Pichia* trace metal (PTM) solution was added aseptically. The PTM solution contained 0.10 g/L biotin, 0.01 g/L $H_3BO_3$, 0.10 g/L $CoCl_2$.6 $H_2O$, 0.30 g/L $CuSO_4$.5 $H_2O$, 32.50 g/L $FeSO_4$.7 $H_2O$, 2.50 ml/L $H_2SO_4$, 1.50 g/L $MnSO_4.H_2O$, 0.04 g/L NaI, 0.10 g/L $Na_2MoO_4$.2 $H_2O$, 10 g/L $ZnCl_2$. The cultivations were controlled under the following conditions: growth temperature 28° C., induction temperature 25° C., aeration 1 win, and absoulte pressure varying between 1 to 2.1 bar. The pH was maintained at 6.0 by the addition of 25% (w/w) ammonia. Except for the induction phase, dissolved oxygen saturation (DO) was maintained above 30% by increasing the stirrer speed from 350 to 610 rpm. After inoculation with 150 ml of pre-culture all fermentations were carried out according to a two-phase strategy: the first phase ended with the depletion of the batch glycerol, indicated by a sharp rise of the DO value resulting in an $OD_{600}$ of ~60±10. Subsequently, the second phase (induction phase) was initiated by adding 0.25% (v/v) methanol. Therefor the fermentation volume was calculated, taking all added solutions and removed sample volumes into account. The resulting resistance read-out was used for the recalibration of the ACETOMAT N II. After recalibration the methanol concentration was kept constant at 0.25% (v/v) using a closed-loop control. The induction was stopped after the addition of a total of ~2700 g of methanol and the fermentation broth was cooled down to temperatures below 20° C. Afterwards the whole broth was harvested and cells were separated from the supernatant by centrifugation in a Beckman Avanti J20 (Beckman Coulter, Brea, Calif., USA) beaker centrifuge (9,000×g for 20 min at 4° C.). The supernatant was collected and stored at −20 C in 800/450 mL-aliquots.

4. Protein Purification

After adjusting the pH to 7.0 the fermentation broth was harvested and centrifuged for 20 min at 4° C., and 9000×g. (Beckmann Avanti J-26 XP). The supernatant was collected for immediate processing or for storage at −20° C.

For subsequent processing/purification two orthogonal chromatography methods were used: immobilized metal ion affinity chromatography (IMAC) as capture step followed by size exclusion chromatography (SEC).

IMAC

To ensure efficient binding of the product during IMAC the supernatant was acclimated to room temperature and if necessary the pH was adjusted to 7.0 with 5 M NaOH. A 0.45/0.2 µm filter (Sartopore 2 150, Sartorius Stedim, Goettlingen) was used to remove particles, thus preventing the chromatography column from blocking.

The conditioned supernatant was loaded onto an equilibrated (200 mM NaCl, 50 mM Na2HPO4, 10 mM Imidazole, pH 7.0), copper charged Chelating Sepharose Fast Flow (GE Healthcare) with a flow rate of 200-250 cm/h. After loading the column was washed with 7 column volumes (CV) of equilibration buffer followed by product elution (200 mM NaCl, 50 mM Na2HPO4, 75-125 mM Imidazole, pH 7.4). Eluates were analyzed by SDS-Page, Coomassie staining and western blot. Finally, appropriate fractions were pooled.

Buffer Exchange

Before running the anion exchange chromatography the buffer of the IMAC eluate was exchanged with 20 mM Tris buffer, pH 8.0 using a HiPrep 26/10 Desalting column (GE-Healthcare, Munich, Germany).

Anion Exchange Chromatography

The previously desalted IMAC eluate was loaded onto an equilibrated (buffer A: 20 mM Tris, pH 8.0) MediaScout® MiniChrom column (ATOLL, Weingarten, Germany) packed with 5 mL Q Sepharose HP (GE-Healthcare, Munich, Germany). Afterwards the column was washed with buffer A followed by a second wash step using 20% buffer B (20 mM Tris, 1 M NaCl, pH8.0). Finally, depending on the vaccine candidate the following concentrations of buffer B were used for the product elution:

TABLE 1

Overview of buffer B concentrations used for the elution of the vaccine candidates.

| Vaccine candidate | Concentration buffer B |
| --- | --- |
| VAMAX 1 | 24% |
| VAMAX 2 | 25-26% |
| VAMAX 6 | 25-26% |

SEC

The IMAC eluate/pool was concentrated 10-30 fold using a Centriprep centrifugal filter unit with a 10 kDa MWCO membrane (Merck Millipore, Darmstadt). Up to 2 ml of the concentrate were loaded onto an equilibrated (2.7 mM KCl, 1.5 mM KH2PO4, 137 mM NaCl, 8.1 mM $Na_2HPO_4$) Sephacryl S-100 HR 16/60 column (GE Healthcare). The product was separated by isocratic elution with equilibration buffer.

5. SDS-PAGE and Immunoblot Analysis

Proteins were separated on commercial 4-12% (w/v) gradient gels (Invitrogen) under non-reducing conditions and stained with Coomassie R-250 following the Fairbanks protocol (Wong et al. 2000). Separated proteins were blotted onto a nitrocellulose membrane (Whatman, Dassel, Germany) and blocked with 5% (w/v) skimmed milk dissolved in PBS. Proteins were probed with the PfAMA1-specific rat mAb4G2 at a 1:5000 dilution. Secondary antibody was Goat anti-rat IgG alkaline phosphatase labeled. Bands were visualized with NBT/BCIP (1 mg·ml-1 in substrate buffer: 150 mM NaCl, 2 mM MgCl2, 50 mM Tris-HCl, pH 9.6). Between the incubation steps the membranes were washed three times with PBS supplemented with 0.05% (v/v) Tween-20.

Figure 3:
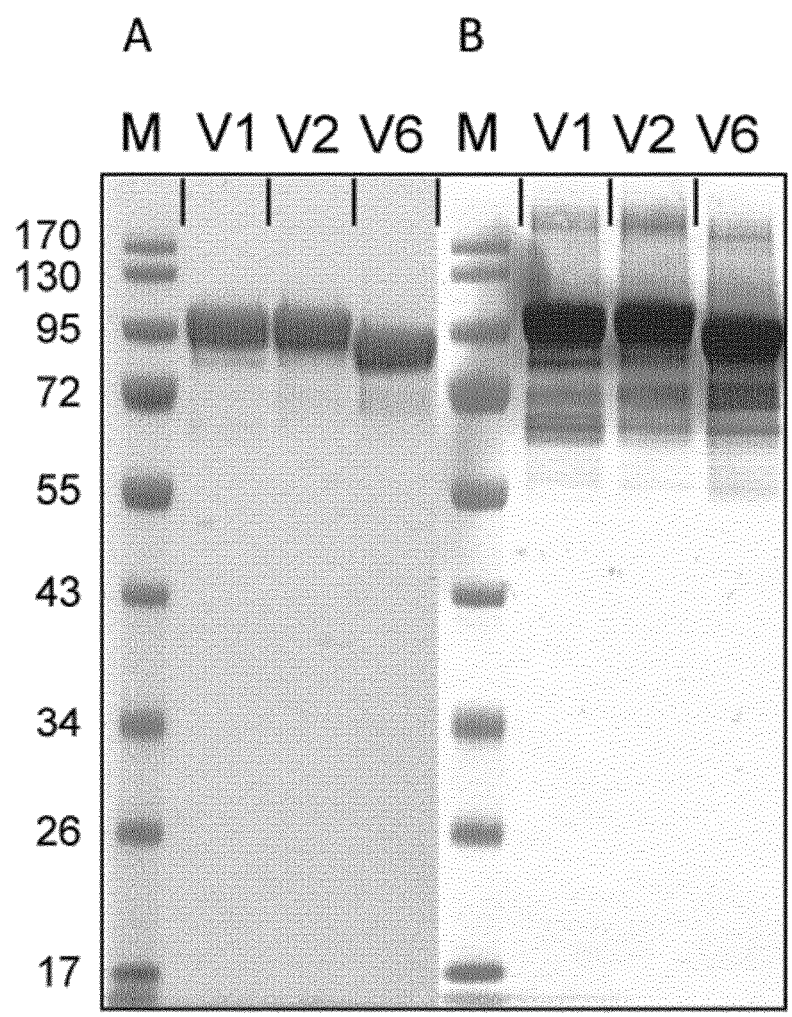
FIG. 3 shows a SDS-PAGE (A) and (B) Western Blot analysis of an embodiment of a vaccine mixture comprising A) the fusion protein 1 with PfAMA1-DICO1, Pfs25 and PfCSP_TSR, B) the fusion protein 2 with PfAMA1-DICO2, Pfs25 and PfMSP1-19, and C) the fusion protein 3 with PfAMA1-DICO3, Pfs25 and PfRh5_Q5A.

FIG. 3 shows the SDS-PAGE (A) and Western Blot analysis (B) of the V1: VAMAX I with PfAMA1-DICO1, Pfs25 and PfCSP_TSR, V2: VAMAX II with PfAMA1-DICO2, Pfs25 and PfMSP1-19, and V3: VAMAX VI with PfAMA1-DICO3, Pfs25 and PfRh5_Q5A. The three fusion proteins are well expressed and can be used for vaccination after isolation. The figure shows that all three fusion proteins were intact and well expressed in yeast.

The abbreviations in FIG. 3 are:
V1: VAMAX I (SEQ ID NO.9)
V2: VAMAX II (SEQ ID NO. 10)
V3: VAMAX VI (SEQ ID NO. 11)
M: Molecular weight marker 6. Immunization of Rabbits The purified proteins (SEQ ID No. 9-11) were mixed (hereinafter called VAMAX-Mix) in equimolar ratio amounts and lyophilized. The recombinant protein mixture was sent to Biogenes (Berlin, Germany) for immunization of rabbits after formulation of 50 µg doses with Alhydrogel (Brenntag) according to the manufacturer's instructions using one prime and two consecutive boost injection (day 28 and 56). Blood samples were taken on day 70.

7. Protein a Purification of Antibodies from Rabbit Sera

After immunization the antibodies from the rabbit antisera were purified by protein A chromatography. Briefly, serum samples were diluted 1:5 with PBS and filtered through 0, 45 µm filter prior purification. The antibodies were bound onto Protein A resin (GE Healthcare) and unbound impurities were removed by a washing step with PBS. The bound antibodies were eluted with 100 mM glycine pH 3.0 and directly neutralized with 1M TRIS pH 8.0. The elution fraction was concentrated to 2.5 ml and buffer exchanged against 5 mM phosphate buffer ph 7.5 (PD10) and lyophilized. The antibody was dissolved in 600 µl PBS and filter sterilzed. Concentration was measured in a 1/20 dilution on the analytical SEC (S200 5/150)

8. Gliding Motility Assay 96-well glass bottom black plates were coated with anti-CSP mAb 3SP2 to capture shed CSP protein. 10.000 *P. falciparum* sporozoites were pre-incubated with rabbit IgG for 30 min and then transferred onto the 3SP2 coated slides. After 90 minutes incubation sporozoites were washed off. Gliding trails were fixed and stained with anti-CSP-biotin followed by streptavidin-AF594. Gliding trails were visualized by fluorescent microscopy at 1000× magnification and images were analyzed with FIJI imaging software.

Figure 4:
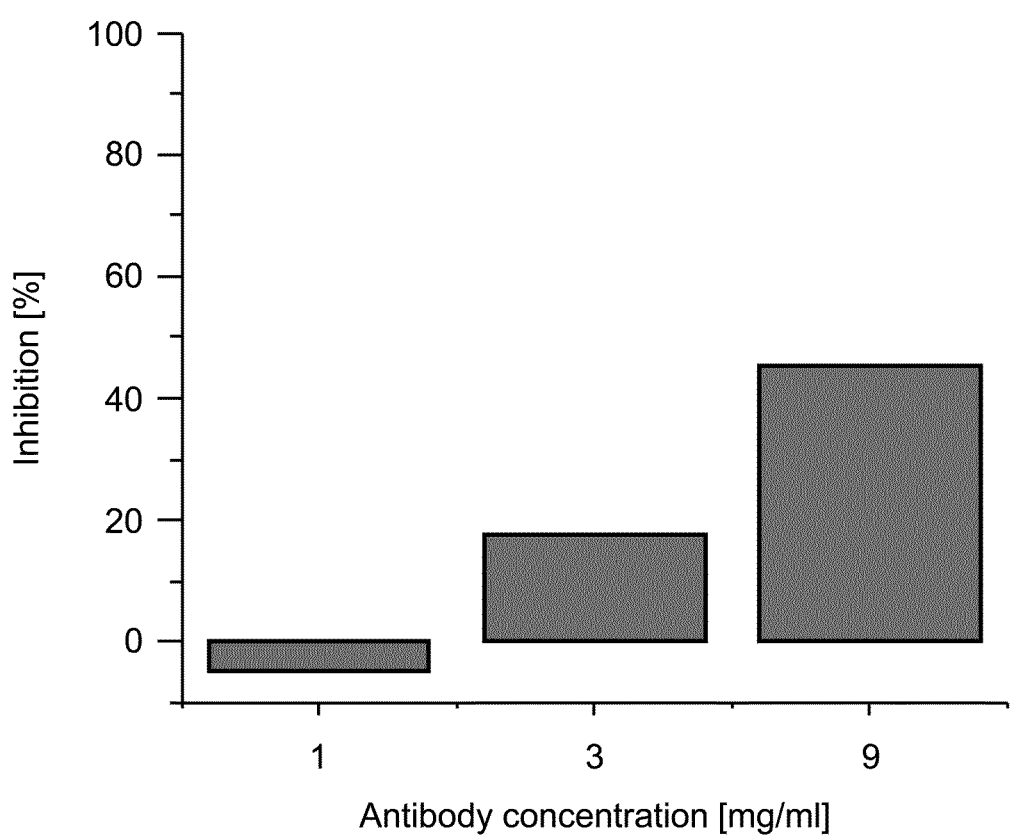
FIG. 4 is a diagram showing the results from the gliding motility assay.

FIG. 4 shows the results from the gliding motility assay. The purified rabbit immune IgG were used at 9, 3 and 1 mg/ml. The plot shows the percent inhibition in relation to antibodies purified from normal rabbit sera. A clear dose-dependency of inhibition was observed.

9. Growth Inhibition Assay

The growth inhibitory potential against *plasmodium* parasites was performed using a standardized protocol. The *P. falciparum* parasite strains 3D7A, HB3, V1-S and 7G8 (provided by MR4) were maintained in culture at parasitemias below 5% at a haematocrit of 4% in RPMI medium supplemented with 10% Albumax II (Invitrogen), 25 mM Hepes, 12 µg/ml gentamicin and 100 µM hypoxanthine at 37° C. and 5% CO2, 5% O2 and 90% N2. The cultures were maintained in a daily routine and parasitemia estimated by Giemsa staining. The erythrocyte used in the assay were mixed from 15 malaria-naïve blood donors and not older than 3 weeks. The erythrocytes were stored in SAG-Mannitol at 4° C. The parasites were synchronized by 10% Sorbitol treatment within a time window of 1-16 hours post invasion. For the assay, only highly synchronous cultures 36 to 40 hours post invasion were used.

Parasites and fresh RBCs and antibodies were mixed in a 96-well plate appropriately in order to have a final parasitemia of 0.1% and a final haematocrit of 2%. For the background control, only RBC without parasites were kept in culture under the same conditions as the parasites. A growth control for the monitoring the parasite growth was performed by culturing the *Plasmodium falciparum* parasite without additions. All samples were measured in triplicates. As negative control, malaria-naïve rabbit and human plasma were derived purified antibodies were tested.

For positive control of complete invasion inhibition, EDTA (4 mM final concentration) and BG98 rabbit anti-AMA-1 polyclonal antibodies were used. The plates were incubated at 37° C., 95% humidity, 5% CO2, 5% O2, and 90% N2 for 40 to 44 hours. At harvest, wells were washed once with cold PBS and frozen down. Parasite growth was estimated by a Malstat™ assay32. Absorbance was measured after 30 minutes at a wavelength of 655 nm using a spectrophotometer. Inhibitory capacity was estimated by the following formula:

$$\% \text{ inhibition} = 100\% - ((A655 \text{ IgG sample} - A655 \text{ RBC control}) / (A655 \text{ Schizont control} - A655 \text{ RBC control})) * 100\%$$

As mentioned above, the growth inhibition assay is a standard in vitro assay to evaluate the inhibitory potential of antibodies. The assay simulates the asexual stage/blood stage.

Figure 5:
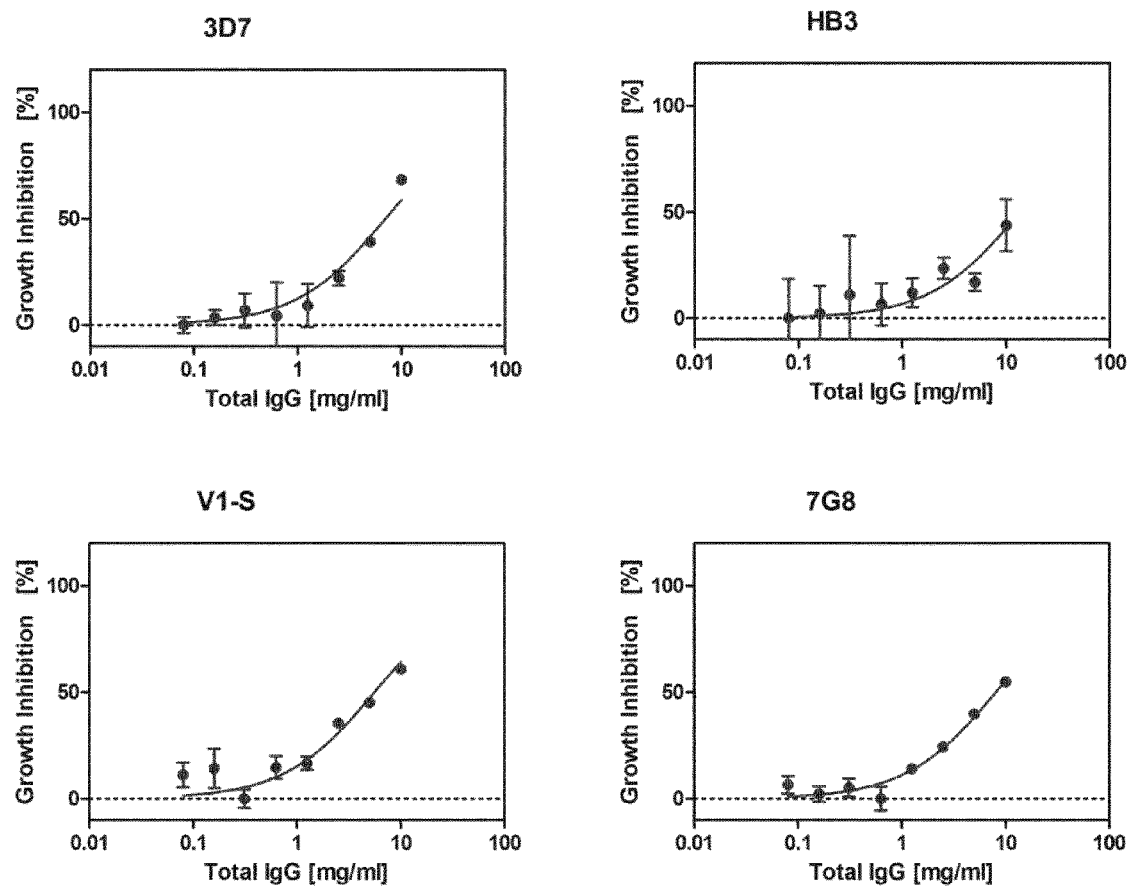
FIG. 5 is a graph showing the results from the growth inhibition assay.

FIG. 5 shows the results from the growth inhibition assay. The purified immune IgG were used at 10, 5, 2.5, 1.25, 0.625, 0.313, 0.156 and 0.078 mg/ml. Parasite growth inhibition from 45% to 68% was observed at 10 mg/ml for all four tested strains (indicated above each graph) confirming the cross-strain efficacy induced by the VAMAX-Mix.

10. Standard Membrane Feeding Assay (SMFA)

The purified IgG samples were combined with stage V gametocytes from *P. falciparum* strain NF54-hsp70-luc, human red blood cells and fed to *Anopheles stephensi* mosquitoes. The experiment was performed in presence of active complement. After 8 days, luciferase expression in individual mosquitoes was analyzed.

Figure 6:
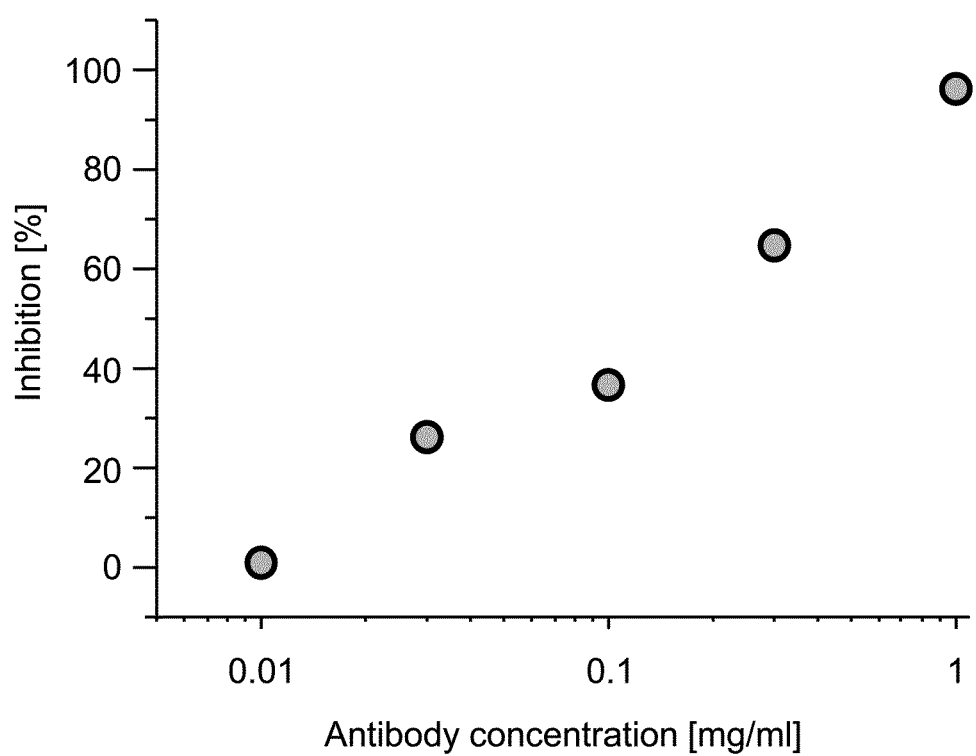
FIG. 6 is a graph showing the results from the Standard membrane feeding assay (SMFA).

FIG. 6 shows the results from the SMFA. The purified rabbit immune IgG were used at 1, 0.3, 0.1, 0.03 and 0.01 mg/ml. The plot shows the percent inhibition in relation to antibodies purified from normal rabbit sera. A clear dose-dependency of inhibition was observed.

REFERENCES

The contents of all cited references, including literature references, issued patents, and published patent applications, as cited throughout this application are hereby expressly incorporated by reference.

Ausubel, F. M. et al. Current protocols in molecular biology, edited by M. Ausubel, R. Brent, R. E. Kingston, D. D. Moore, J. G. Seidman, J. A. Smith, and K. Struhl. Volumes 1 and 2. John Wiley & Sons, Inc., Media, P A, 1988, 165.00. Molecular Reproduction and Development 1, 146-146 (1989).

Cregg J M, Cereghino J L, Shi J, Higgins D R. 2000. Recombinant protein expression in *Pichia pastoris*. Mol. Biotechnol. 16:23-52.

Douglas AD1, Williams A R, Knuepfer E, Illingworth J J, Furze J M, Crosnier C, Choudhary P, Bustamante L Y, Zakutansky S E, Awuah D K, Alanine D G, Theron M, Worth A, Shimkets R, Rayner J C, Holder A A, Wright G J, Draper S J. 2014. Neutralization of *Plasmodium falci-* parum merozoites by antibodies against PfRH5. J Immunol. 2014 Jan. 1; 192(1):245-58. doi: 10.4049/jimmunol.1302045. Epub 2013 Nov. 29.

Drickamer K, Taylor M E (2006). *Introduction to Glycobiology* (2nd ed.). Oxford University Press, USA. ISBN 978-O-19-928278-4.

Gosselin, E. J., K. Wardwell, D. R. Gosselin, N. Alter, J. L. Fisher, and P. M. Guyre. 1992. Enhanced antigen presentation using human Fc gamma receptor (monocyte/macrophage)-specific immunogens. J. Immunol. 149:3477-3481.

Mahajan, B., J. A. Berzofsky, et al. (2010). "Multiple antigen peptide vaccines against *Plasmodium falciparum* malaria." Infect Immun 78(11): 4613-4624.

Remarque E J E, Faber B W B, Kocken C H M C, Thomas A W A (2008) A diversity-covering approach to immunization with *Plasmodium falciparum* apical membrane antigen 1 induces broader allelic recognition and growth inhibition responses in rabbits. Infect Immun 76: 2660-2670. doi:10.1128/IAI.00170-08.

Richards, J. S. and J. G. Beeson (2009). "The future for blood-stage vaccines against malaria." Immunol Cell Biol 87(5): 377-390.

Sambrook, J., Fritsch, E. F. & Maniatis, T. Molecular Cloning: A Laboratory Manual, Volume 1 to 3, 2nd edition. Sambrook J E F Fritsch and T Maniatis Molecular Cloning A Laboratory Manual Second Edition Vols 1 2 and 3 Cold Spring Harbor Laboratory Press Cold Spring Harbor N.Y. USA Illus Paper (1989).

Schwartz, L., G. V. Brown, et al. (2012). "A review of malaria vaccine clinical projects based on the WHO rainbow table." Malar J 11: 11.

Taylor, W. R. The classification of amino acid conservation. Journal of theoretical biology 119, 205-18 (1986).

Tucker R. P. 2004. The thrombospondin type 1 repeat family. Int. J. Biochem. Cell Biol. 36: 969-974.

Wong C, Sridhara S, Bardwell J C, Jakob U. 2000. Heating greatly speeds Coomassie blue staining and destaining. Biotechniques 28(3):426-8, 430, 432.

---

What is claimed is:

1. A mixture of recombinant proteins as an immunogenic composition for inducing an immune response in a human against the parasite *Plasmodium falciparum*, wherein the mixture comprises:
   a) a first recombinant fusion protein (fusion protein 1) comprising PfAMA1-DICO1, Pfs25 and PfCSP_TSR;
   b) a second recombinant fusion protein (fusion protein 2) comprising PfAMA1-DICO2, Pfs25 and PfMSP1-19; and
   c) a third recombinant fusion protein (fusion protein 3) comprising PfAMA1-DICO3, Pfs25 and a PfRh5 peptide.

2. The mixture according to claim 1, wherein the recombinant fusion proteins are in equimolar ratios in the mixture.

3. The mixture according to claim 1, further comprising an adjuvant.

4. The mixture according to claim 1, wherein:
   a) fusion protein 1 comprises the amino acid sequence of SEQ ID NO. 9;
   b) fusion protein 2 comprises the amino acid sequence of SEQ ID NO. 10; and
   c) fusion protein 3 comprises the amino acid sequence of SEQ ID NO. 11.

5. The mixture according to claim 1, wherein:
   a) fusion protein 1 comprises the amino acid sequence of SEQ ID NO. 9;
   b) fusion protein 2 comprises the amino acid sequence of SEQ ID NO. 10; and
   c) fusion protein 3 comprises the amino acid sequence of SEQ ID NO. 12.

* * * * *